United States Patent
Berg et al.

(10) Patent No.: US 6,475,222 B1
(45) Date of Patent: Nov. 5, 2002

(54) MINIMALLY INVASIVE REVASCULARIZATION APPARATUS AND METHODS

(75) Inventors: Todd Allen Berg, Plymouth, MN (US); Daniel J. Sullivan, Medina, MN (US); Matthew W. Baker, Minneapolis, MN (US); Paul J. Hindrichs, Plymouth, MN (US); Gregory Alan Boldenow, Crystal, MN (US); Jason A. Galdonik, Minneapolis, MN (US); Mark D. Wahlberg, St. Paul, MN (US)

(73) Assignee: St. Jude Medical ATG, Inc., Minneapolis, MN (US)

( * ) Notice: Subject to any disclaimer, the term of this patent is extended or adjusted under 35 U.S.C. 154(b) by 0 days.

(21) Appl. No.: 09/187,364

(22) Filed: Nov. 6, 1998

(51) Int. Cl.[7] .............................. A61B 1/04; A61B 1/06
(52) U.S. Cl. ..................... 606/108; 606/170; 606/185; 623/1.23
(58) Field of Search ................... 606/108, 185, 606/198, 190, 192, 194, 195, 159, 158, 170; 604/280, 281, 282, 283, 170, 171, 96; 623/1.14, 1.23, 1.13, 1.21, 1.35, 1.36

(56) References Cited

U.S. PATENT DOCUMENTS

| | | | |
|---|---|---|---|
| 3,903,892 A | 9/1975 | Komiya ................ 128/303.15 |
| 3,908,662 A | 9/1975 | Razgulov et al. | |
| 4,041,931 A | * 8/1977 | Elliott et al. .................... 128/1 |
| 4,214,586 A | 7/1980 | Mericle | |
| 4,214,587 A | 7/1980 | Sakura, Jr. .............. 128/334 R |
| 4,366,819 A | 1/1983 | Kaster | |
| 4,368,736 A | 1/1983 | Kaster | |
| 4,418,693 A | 12/1983 | LeVeen ................... 128/303 R |
| 4,459,252 A | 7/1984 | MacGregor ................ 264/46.9 |
| 4,469,483 A | * 9/1984 | Becker et al. ............... 604/280 |
| 4,503,569 A | 3/1985 | Dotter ............................. 3/1.4 |
| 4,523,592 A | 6/1985 | Daniel | |
| 4,568,334 A | * 2/1986 | Lynn ........................... 604/171 |
| 4,592,754 A | 6/1986 | Gupte et al. ..................... 623/1 |
| 4,605,406 A | 8/1986 | Cahalan et al. ................. 623/1 |
| 4,617,932 A | 10/1986 | Kornberg ................ 128/334 R |
| 4,629,458 A | 12/1986 | Pinchuk ......................... 623/1 |
| 4,632,842 A | 12/1986 | Karwoski et al. ............... 427/2 |
| 4,651,733 A | 3/1987 | Mobin-Uddin .......... 128/303 R |
| 4,657,019 A | 4/1987 | Walsh et al. | |
| 4,665,906 A | 5/1987 | Jervis ..................... 128/92 YN |
| 4,665,918 A | 5/1987 | Garza et al. ................. 128/343 |
| 4,696,308 A | 9/1987 | Meller et al. | |

(List continued on next page.)

FOREIGN PATENT DOCUMENTS

| | | | |
|---|---|---|---|
| WO | WO 98/19618 | 5/1998 | ........... A61B/19/00 |
| WO | WO 98/19629 | 5/1998 | ............. A61F/2/06 |
| WO | WO 98/19634 | 5/1998 | ............. A61F/2/06 |
| WO | WO 98/19635 | 5/1998 | ............. A61F/2/06 |
| WO | WO 99/62408 | 12/1999 | |

Primary Examiner—Cary E. O'Connor
(74) Attorney, Agent, or Firm—Fish & Neave; Robert R. Jackson; Brajesh Mohan

(57) ABSTRACT

A bypass graft conduit is installed in the circulatory system of a patient using apparatus which facilitates performing most or all of the necessary work intraluminally (i.e., via lumens of the patient's circulatory system). A guide structure such as a wire is installed in the patient via circulatory system lumens so that a portion of the guide structure extends along the desired path of the bypass conduit, which bypass conduit path is outside the circulatory system as it exists prior to installation of the bypass graft. The bypass graft is then introduced into the patient along the guide structure and connected at each of its ends to the circulatory system using connectors that form fluid-tight annular openings from the bypass graft lumen into the adjacent circulatory system lumens. The guide structure is then pulled out of the patient.

92 Claims, 25 Drawing Sheets

U.S. PATENT DOCUMENTS

| | | | |
|---|---|---|---|
| 4,705,517 A | 11/1987 | DiPisa, Jr. | 623/12 |
| 4,718,907 A | 1/1988 | Karwoski et al. | 623/12 |
| 4,733,665 A | 3/1988 | Palmaz | 128/343 |
| 4,738,740 A | 4/1988 | Pinchuk et al. | 156/167 |
| 4,743,252 A | 5/1988 | Martin, Jr. et al. | 623/1 |
| 4,748,984 A | 6/1988 | Patel | 128/658 |
| 4,787,899 A | 11/1988 | Lazarus | 623/1 |
| 4,795,458 A | 1/1989 | Regan | 623/1 |
| 4,798,606 A | 1/1989 | Pinchuk | 623/1 |
| 4,832,028 A * | 5/1989 | Patel | 128/344 |
| 4,892,539 A | 1/1990 | Koch | 623/1 |
| 4,969,890 A | 11/1990 | Sugita et al. | 606/192 |
| 5,007,919 A * | 4/1991 | Silva et al. | 606/194 |
| 5,035,702 A | 7/1991 | Taheri | 606/153 |
| 5,037,377 A | 8/1991 | Alonso | 600/36 |
| 5,061,245 A | 10/1991 | Waldvogel | 604/170 |
| 5,061,275 A | 10/1991 | Wallsten et al. | 623/1 |
| 5,084,065 A | 1/1992 | Weldon et al. | 623/1 |
| 5,104,399 A | 4/1992 | Lazarus | 623/1 |
| 5,116,317 A * | 5/1992 | Carson, Jr. et al. | 606/191 |
| 5,116,360 A | 5/1992 | Pinchuk et al. | 623/1 |
| 5,122,154 A | 6/1992 | Rhodes | 606/198 |
| 5,147,370 A | 9/1992 | McNamara et al. | 606/108 |
| 5,163,951 A | 11/1992 | Pinchuk et al. | 623/1 |
| 5,171,232 A * | 12/1992 | Castillo et al. | 604/280 |
| 5,171,233 A | 12/1992 | Amplatz et al. | 604/281 |
| 5,176,693 A * | 1/1993 | Pannek, Jr. | 606/159 |
| 5,201,901 A | 4/1993 | Harada et al. | 606/198 |
| 5,209,731 A | 5/1993 | Sterman et al. | 604/97 |
| 5,211,658 A | 5/1993 | Clouse | 623/1 |
| 5,211,683 A * | 5/1993 | Maginot | 606/159 |
| 5,226,429 A | 7/1993 | Kuzmak | 128/898 |
| 5,234,447 A | 8/1993 | Kaster et al. | 606/153 |
| 5,234,448 A | 8/1993 | Wholey et al. | 606/153 |
| 5,250,058 A | 10/1993 | Miller et al. | 606/154 |
| 5,250,059 A * | 10/1993 | Andreas et al. | 606/159 |
| 5,254,088 A * | 10/1993 | Lundquist et al. | 604/95 |
| 5,256,150 A | 10/1993 | Quiachon et al. | 604/171 |
| 5,261,878 A * | 11/1993 | Galindo | 606/194 |
| 5,275,622 A | 1/1994 | Lazarus et al. | 623/1 |
| 5,287,861 A | 2/1994 | Wilk | 128/898 |
| 5,297,564 A | 3/1994 | Love | 128/898 |
| 5,304,220 A | 4/1994 | Maginot | 623/1 |
| 5,306,240 A | 4/1994 | Berry | 604/51 |
| 5,312,343 A * | 5/1994 | Krog et al. | 606/197 |
| 5,314,418 A * | 5/1994 | Takano et al. | 604/282 |
| 5,316,023 A | 5/1994 | Palmaz et al. | 128/898 |
| 5,334,217 A | 8/1994 | Das | 606/213 |
| 5,345,937 A * | 9/1994 | Middleman et al. | 604/280 |
| 5,354,309 A | 10/1994 | Schnepp-Pesch et al. | 606/198 |
| 5,356,382 A * | 10/1994 | Picha et al. | 606/198 |
| 5,360,443 A | 11/1994 | Barone et al. | 623/1 |
| 5,366,464 A * | 11/1994 | Belknap | 606/159 |
| 5,366,504 A | 11/1994 | Andersen et al. | 623/11 |
| 5,387,235 A | 2/1995 | Chuter | 623/1 |
| 5,395,349 A | 3/1995 | Quiachon et al. | 604/248 |
| 5,397,345 A | 3/1995 | Lazarus | 623/1 |
| 5,409,019 A | 4/1995 | Wilk | 128/898 |
| 5,419,324 A | 5/1995 | Dillow | 128/653.1 |
| 5,425,765 A | 6/1995 | Tiefenbrun et al. | 623/12 |
| 5,429,144 A | 7/1995 | Wilk | 128/898 |
| 5,431,673 A * | 7/1995 | Summers et al. | 606/170 |
| 5,433,727 A | 7/1995 | Sideris | 606/213 |
| 5,437,288 A | 8/1995 | Schwartz et al. | 128/772 |
| 5,443,497 A * | 8/1995 | Venbrux | 623/1 |
| 5,443,499 A | 8/1995 | Schmitt | 623/1 |
| 5,452,733 A | 9/1995 | Sterman et al. | 128/898 |
| 5,453,090 A * | 9/1995 | Martinez et al. | 606/108 |
| 5,456,712 A | 10/1995 | Maginot | 623/1 |
| 5,458,615 A * | 10/1995 | Klemm et al. | 606/198 |
| 5,480,423 A | 1/1996 | Ravenscroft et al. | 623/1 |
| 5,484,418 A | 1/1996 | Quiachon et al. | 604/167 |
| 5,489,295 A | 2/1996 | Piplani et al. | 623/1 |
| 5,496,364 A | 3/1996 | Schmitt | 623/1 |
| 5,496,365 A | 3/1996 | Sgro | 623/1 |
| 5,507,769 A | 4/1996 | Marin et al. | 606/198 |
| 5,509,931 A | 4/1996 | Schmitt | 623/1 |
| 5,522,834 A | 6/1996 | Fonger et al. | 606/194 |
| 5,522,880 A | 6/1996 | Barone et al. | 623/1 |
| 5,527,337 A * | 6/1996 | Stack et al. | 606/198 |
| 5,542,944 A | 8/1996 | Bhatta | 606/33 |
| 5,545,214 A | 8/1996 | Stevens | 623/2 |
| 5,549,663 A | 8/1996 | Cottone | 623/1 |
| 5,554,152 A | 9/1996 | Aita et al. | 606/7 |
| 5,554,163 A * | 9/1996 | Shturman | 606/159 |
| 5,562,725 A | 10/1996 | Schmitt et al. | 623/1 |
| 5,562,728 A | 10/1996 | Lazarus et al. | 623/1 |
| 5,571,172 A | 11/1996 | Chin | 623/1 |
| 5,584,875 A | 12/1996 | Duhamel et al. | 623/1 |
| 5,628,788 A | 5/1997 | Pinchuk | 623/1 |
| 5,632,772 A | 5/1997 | Alcime et al. | 623/1 |
| 5,645,556 A * | 7/1997 | Yoon | 606/185 |
| 5,653,747 A | 8/1997 | Dereume | 623/1 |
| 5,676,670 A | 10/1997 | Kim | 606/108 |
| 5,695,504 A | 12/1997 | Gifford, III et al. | 606/153 |
| 5,749,879 A * | 5/1998 | Middleman et al. | 606/139 |
| 5,830,222 A | 11/1998 | Makower | 606/159 |
| 5,833,658 A * | 11/1998 | Levy et al. | 606/108 |
| 5,843,103 A * | 12/1998 | Wulfman | 606/180 |
| 5,868,763 A | 2/1999 | Spence et al. | 606/153 |
| 5,876,408 A * | 3/1999 | Alt et al. | 606/129 |
| 5,893,369 A | 4/1999 | LeMole | 606/184 |
| 5,908,448 A * | 6/1999 | Roberts et al. | 623/1 |
| 5,916,194 A * | 6/1999 | Jacobsen et al. | 604/96 |
| 5,921,958 A * | 7/1999 | Resseman et al. | 606/194 |
| 5,968,068 A * | 10/1999 | Dehdashtian et al. | 606/192 |
| 5,976,159 A | 11/1999 | Bolduc et al. | 606/142 |
| 5,976,178 A | 11/1999 | Goldsteen et al. | |
| 6,026,814 A | 2/2000 | LaFontaine et al. | 128/898 |
| 6,035,856 A | 3/2000 | LaFontaine et al. | 128/898 |
| 6,193,734 B1 | 2/2001 | Bolduc et al. | 606/153 |

* cited by examiner

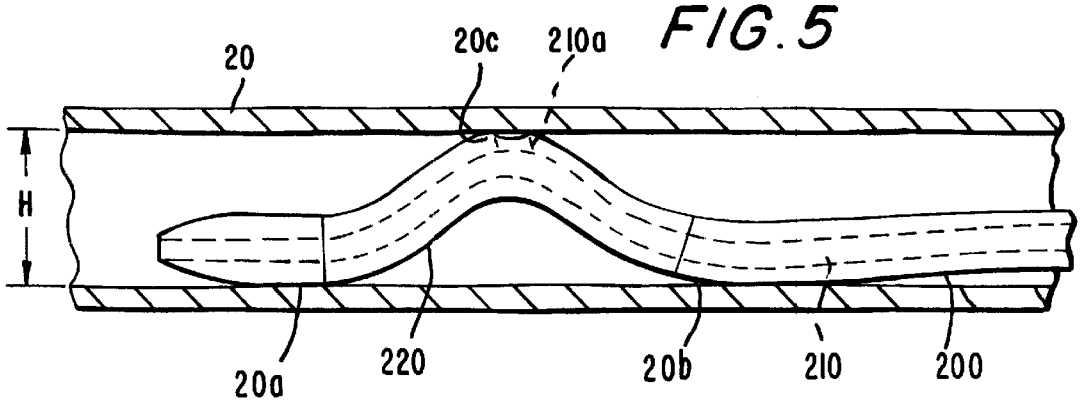
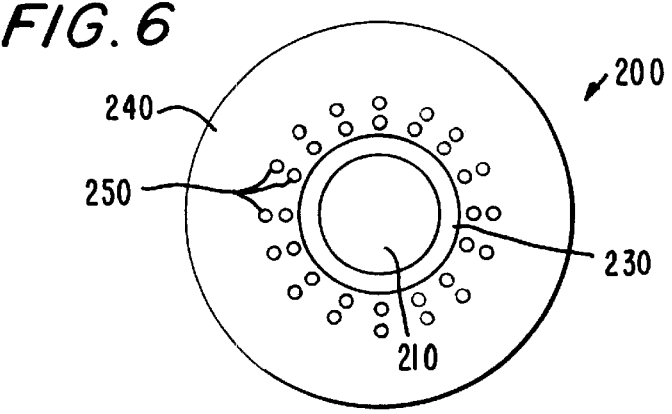
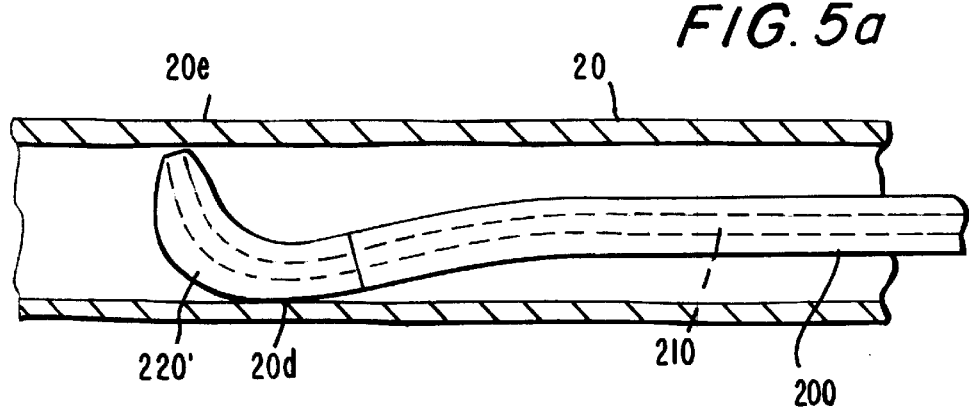

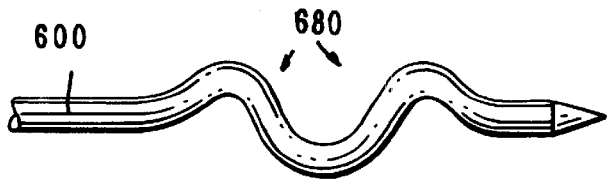
FIG. 20a
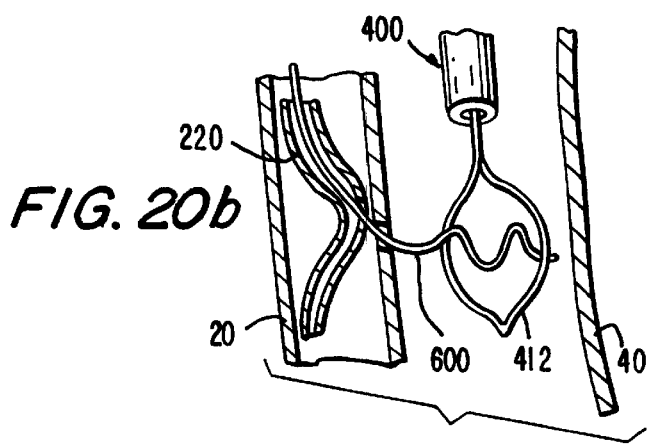
FIG. 20b
FIG. 21a
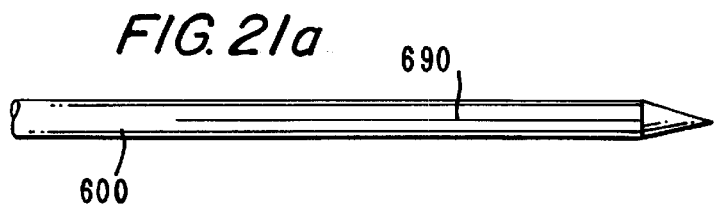
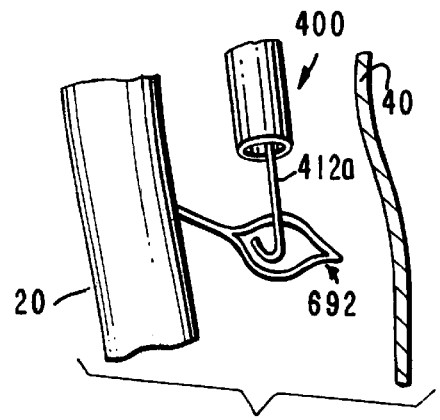
FIG. 21b
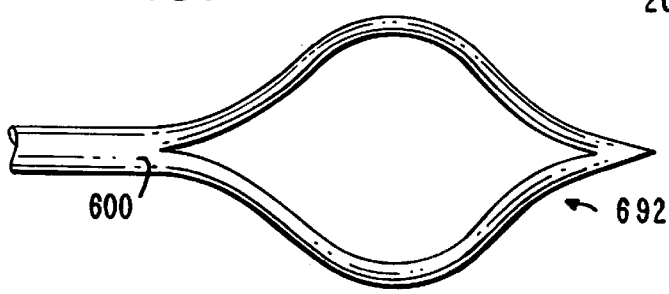
FIG. 21c

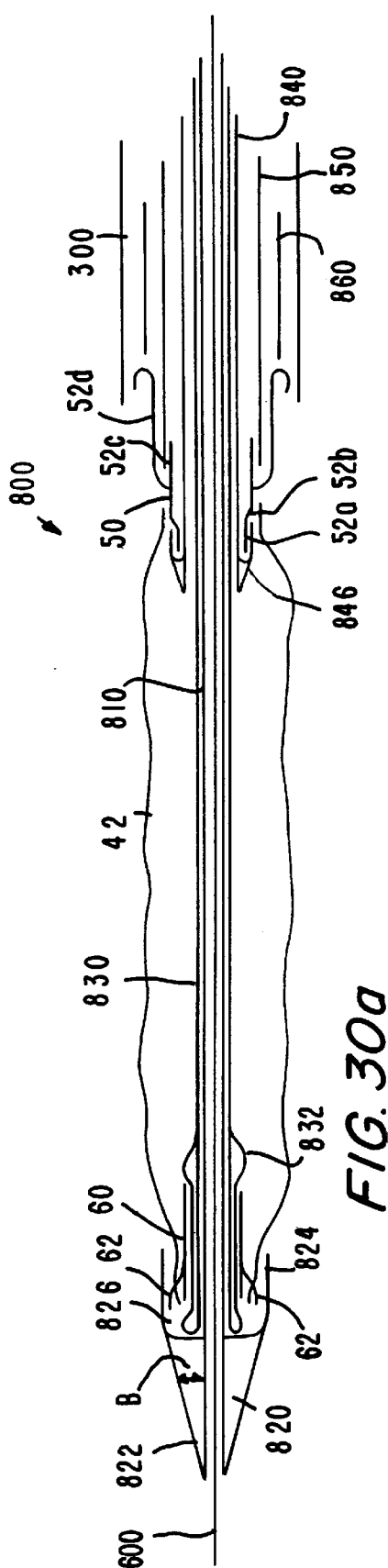
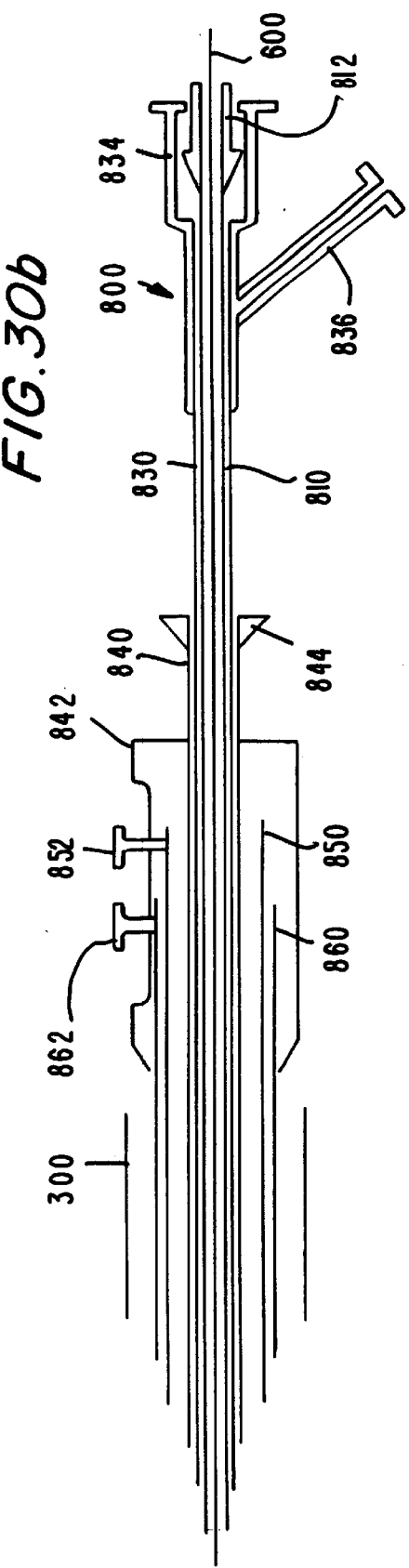
FIG. 30a
FIG. 30b

MINIMALLY INVASIVE REVASCULARIZATION APPARATUS AND METHODS

BACKGROUND OF THE INVENTION

This invention relates to medical apparatus and methods, and more particularly to apparatus and methods for installing a tubular graft in a patient for such purposes as bypassing an occlusion in the patient's tubular body conduit structure.

Goldsteen et al. U.S. patent application Ser. No. 08/745,618, filed Nov. 7, 1996, which is hereby incorporated by reference herein in its entirety, shows, among other things, apparatus and methods for installing a graft conduit in a patient, with most or all of the work being done intraluminally through the patient's existing body conduit structure. Testing and further development work have suggested that it would be advantageous to improve and/or augment some aspects of apparatus and/or methods of the kind shown an the above-mentioned Goldsteen et al. reference.

In view of the foregoing, it is an object of this invention to improve and simplify various aspects of apparatus and methods of the general type shown in the above-mentioned Goldsteen et al. reference.

It is another object of this invention to provide additional and/or alternative apparatus and/or methods for certain aspects of technology of the general type shown in the Goldsteen et al. reference.

SUMMARY OF THE INVENTION

These and other objects of the invention are accomplished in accordance with the principles of the invention by providing improved apparatus and methods for installing a guide structure in a patient between two locations along the patient's circulatory system that are to be connected by a bypass graft. The guide structure extends between those two locations outside the circulatory system (albeit within the patient) and is used to guide the bypass graft into place between those two locations. The guide structure is preferably installed in the patient intraluminally (i.e., via lumens of the patient's circulatory system), although there is a portion of the guide structure which ultimately extends outside the circulatory system as mentioned above. A portion of the guide structure may be re-routable in the circulatory system to improve the alignment of the guide structure for purposes of optimal guidance of the bypass graft into place. For example, the guide structure may be re-routed so that, whereas both ends of the guide structure initially extend out of the patient, only one end of the re-routed guide structure extends out of the patient, while the other end of the guide structure dead-ends in the patient. Again, the new routing of the guide structure may improve its ability to guide the bypass graft into a desired alignment in the patient.

Improved apparatus and methods for delivering a bypass graft conduit into the patient along the guide structure are also provided. For example, the graft delivery structure may include a very gradually tapered distal nose portion to facilitate entry of the apparatus into the patient's circulatory system at one end of the graft installation site. Improved connectors for attaching one or both ends of the graft conduit to the patient's circulatory system may also be used.

Further features of the invention, its nature and various advantages will be more apparent from the accompanying drawings and the following detailed description of the preferred embodiments.

BRIEF DESCRIPTION OF THE DRAWINGS

FIG. 5 is a simplified enlargement of a portion of FIG. 4.

FIG. 5a is another view similar to FIG. 5 showing an alternative embodiment of the FIG. 5 apparatus.

FIG. 6 is a simplified cross sectional view of an illustrative embodiment of a portion of the FIG. 5 apparatus in accordance with the invention.

FIGS. 5a–e are simplified elevational views of components of an illustrative embodiment of a portion of the apparatus shown in FIG. 14.

FIG. 15f is a simplified elevational view taken along the line 15f—15f in FIG. 15a.

FIG. 20a is a simplified elevational view illustrating another possible feature of a portion of the apparatus shown, for example, in FIG. 17 in accordance with the invention.

FIG. 20b is another view similar to FIG. 17 showing use of the FIG. 20a feature in accordance with the invention.

FIG. 21a is another view similar to FIG. 20a illustrating an alternative possible feature of a portion of the apparatus shown, for example, in FIG. 17 in accordance with the invention.

FIG. 21b is another view similar to FIG. 21a showing another operating condition of the FIG. 21a apparatus.

FIG. 21c is another view similar to FIG. 17 showing use of the FIG. 21a–b feature in accordance with the invention.

FIGS. 30a and 30b collectively comprise a simplified sectional view of an illustrative embodiment of further apparatus in accordance with the invention.

FIGS. 30a and 30b are sometimes referred to collectively as FIG. 30.

DETAILED DESCRIPTION OF THE PREFERRED EMBODIMENTS

Although the invention has other possible uses, the invention will be fully understood from the following explanation of its use in providing a bypass around an obstruction in a patient's vascular system.

Figure 1:
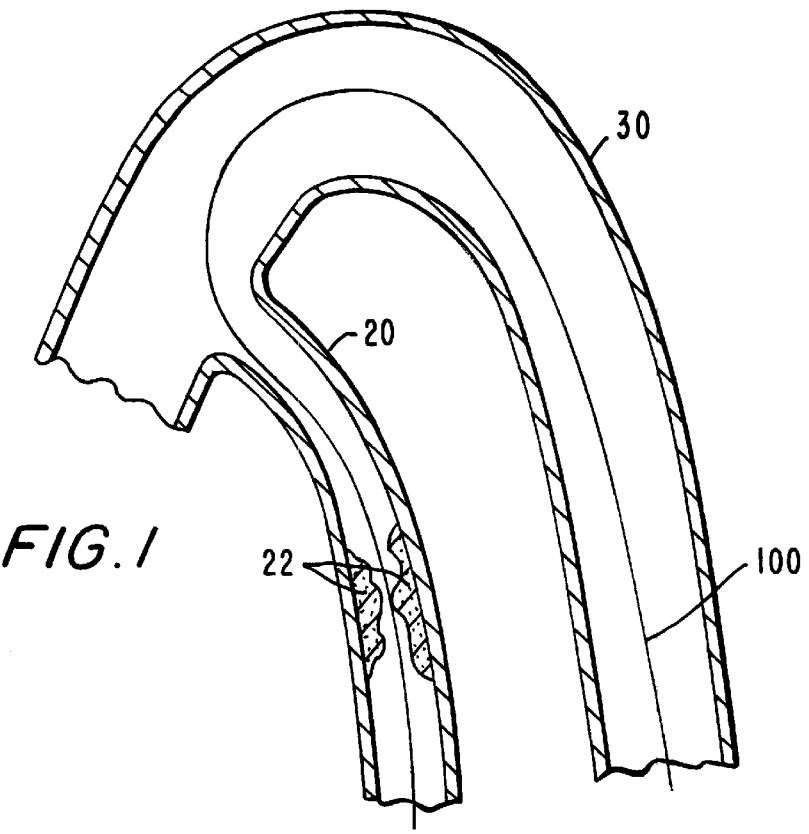
FIG. 1 is a simplified sectional view showing an early stage in use of illustrative apparatus and methods in accordance with this invention.

As shown in FIG. 1, an early stage in an illustrative coronary artery bypass procedure in accordance with the invention includes introducing a longitudinal guide member 100 (typically a guide wire, and therefore sometimes referred to as such herein) into the patient's circulatory system across the coronary artery occlusion 22 to be bypassed. For example, guide wire 100 may be introduced into the patient via a femoral (leg) artery (not shown). From the femoral artery, guide wire 100 may be pushed intraluminally into the patient's aorta 30, and from the aorta into the coronary artery 20 that has occlusion 22. Advancement of guide wire 100 may be stopped at any desired point after the distal portion of the guide wire has passed through occlusion 22.

Figure 2:
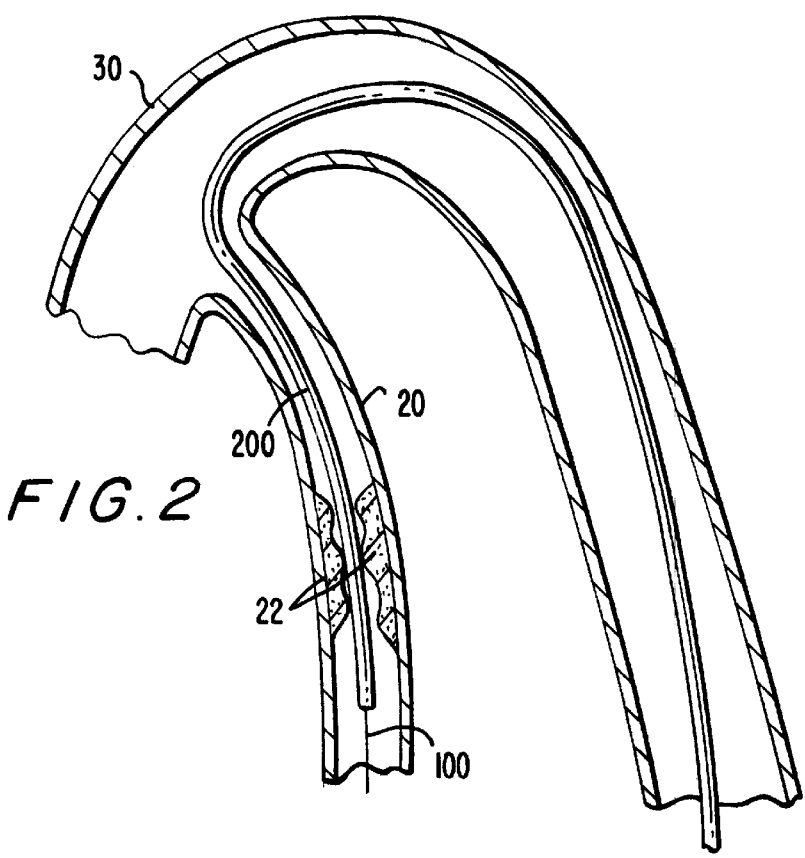
FIG. 2 is a view similar to FIG. 1 showing a later stage in use of illustrative apparatus and methods in accordance with the invention.
Figure 3:
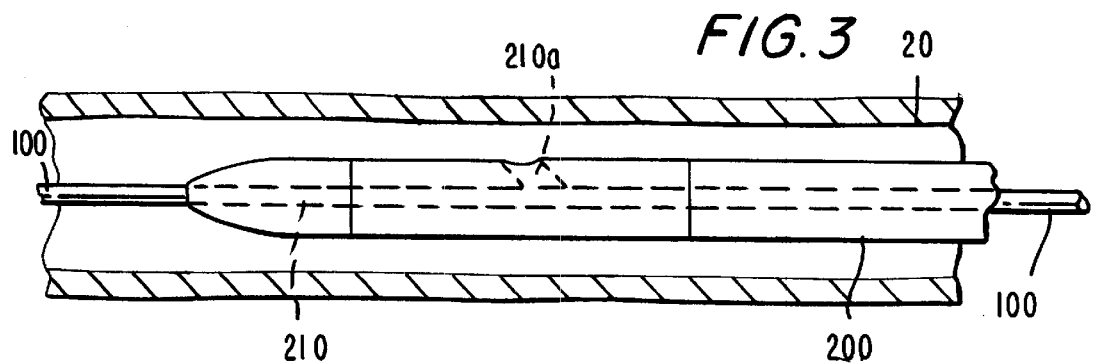
FIG. 3 is a simplified enlargement of a portion of FIG. 2.

After guide wire 100 is across occlusion 22 as shown in FIG. 1, a catheter or catheter-like structure 200 is introduced into the patient along guide wire 100 as shown in FIG. 2. A more detailed view of a distal portion of catheter 200 is shown in FIG. 3, wherein it can be seen that the catheter has an axially extending lumen 210 for containing guide wire 100 as the catheter is advanced along the guide wire. Guide wire 100 facilitates passage of the distal portion of catheter 200 through occlusion 22 as shown in FIG. 2.

After the distal portion of catheter 200 has passed through occlusion 22 as shown in FIG. 2, guide wire 100 is pulled proximally out of the catheter and out of the patient.

Figure 4:
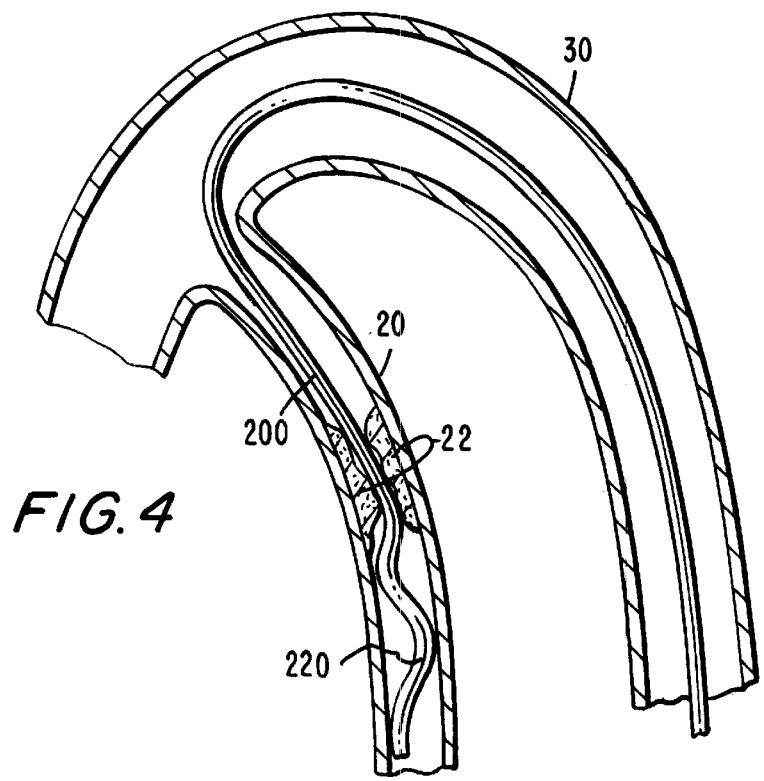
FIG. 4 is a view similar to FIG. 2 showing a still later stage in use of illustrative apparatus and methods in accordance with the invention.

A medial portion 220 of catheter 200 is preferably constructed to form a laterally extending arch as shown in FIGS. 4 and 5 when guide wire 100 is withdrawn from the catheter. For example, catheter 200 may be made so that it resiliently tends to form an arch of a predetermined lateral extent when it is freed from the straightening effect of guide wire 100. The arch height H may be specifically designed to complement various artery sizes (e.g., 3.0 mm, 3.5 mm, 4.0 mm, etc., diameter vessels). For example, the arch height may be selected to be approximately the same as or slightly greater than the inside diameter of the artery 20 into which the catheter will be inserted. In this way the bases of the arch (in contact with one side of the interior of the artery wall at axially spaced locations 20a and 20b) will push the apex of the arch against the diametrically opposite side of the artery wall (at location 20c, which is axially medial locations 20a and 20b).

Figure 17:
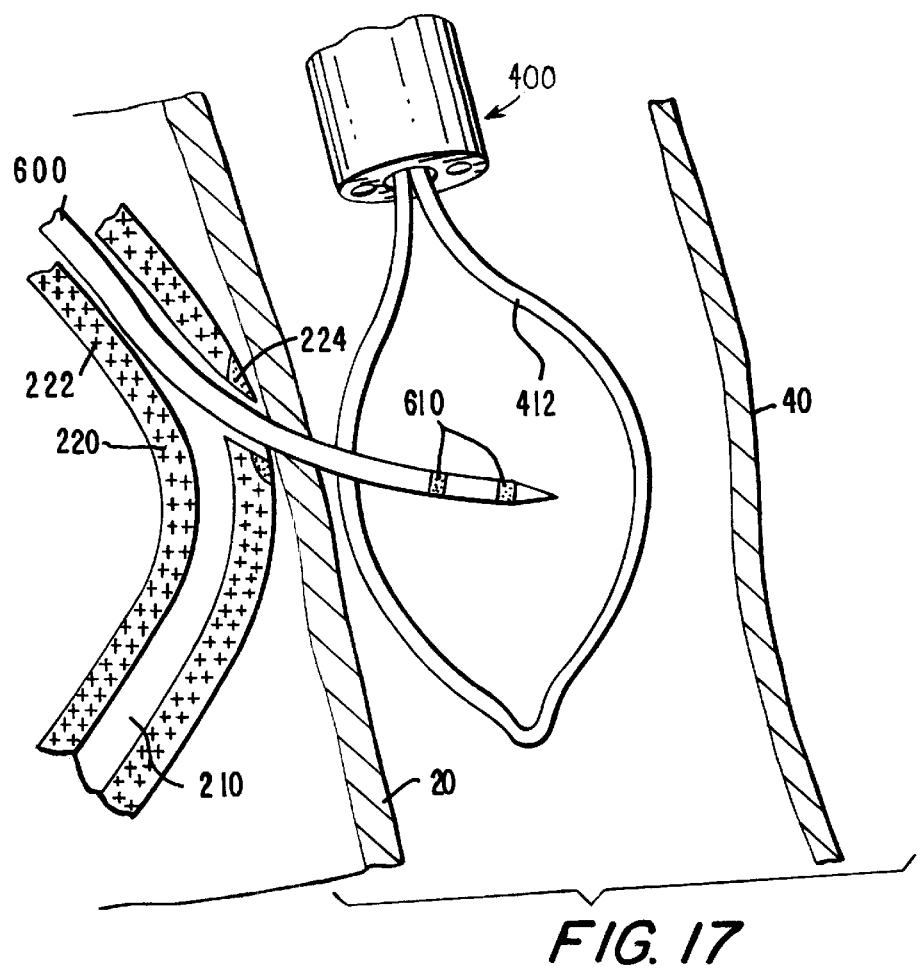
FIG. 17 is a more detailed view similar to a portion of FIG. 16.

The lumen 210 in catheter 200 has a side branch 210a which exits from the side wall of the catheter at or near the apex of the above-described arch in the catheter. Catheter portion 220, which forms the above-described arch, is preferably loaded with conventional radio-opaque filler (e.g., as indicated by the small plus signs in FIG. 17) to help the physician using the apparatus to radiologically locate and properly orient catheter portion 220 in the patient's artery. Portions of catheter 200 which are distal and proximal of portion 220 may be less radio-opaque to help highlight portion 220. The objective is to position lumen branch 210a at the approximate location along artery 20 at which it is desired to connect one end of a bypass graft to the artery. Radiologic observation may be further aided by providing a radiologically viewable (e.g., radio-opaque) marker band around the exit from lumen branch 210a (e.g., as shown at 224 in FIG. 17). (As a general matter, the term "radiologic" is frequently used herein as a generic term for any kind of radiologically viewable (e.g., radio-opaque) material or structure.)

Additional details of preferred constructional features of catheter 200 are shown in the typical cross sectional view of FIG. 6. As shown in FIG. 6 the catheter tube preferably has an inner liner 230 of polytetrafluoroethylene to minimize internal friction. A reinforcing layer such as a braid of wires 250 may be included to enable the catheter to transmit torque and to provide kink resistance. Polymer layer 240 (e.g., Pebax or nylon) provides support and curve retention. Internal lumen 210 preferably extends along the entire length of the catheter and is used to allow the catheter to track over guide wire 100 as described above, and to subsequently guide a longitudinal piercing structure to the point on the wall of artery 20 where it is desired to connect one end of a bypass graft. (The piercing structure and its use will be described in more detail shortly.) The distal tip portion of catheter 200 may be made especially soft and/or the external surface of the catheter may be coated with polytetrafluoroethylene to enhance the ability of the catheter to pass through an occlusion like occlusion 22. A soft tip also helps make catheter 200 atraumatic. The distal tip portion of the catheter may be tapered in the distal direction or similar reasons. Overall, the transverse dimensions of catheter 200 are preferably made small (e.g., less than 3 French or 1.0 mm) to facilitate introduction of the catheter into the patient, especially a relatively small coronary artery and the even smaller passageway through the occlusion 22 in that artery. Although polytetrafluoroethylene has been mentioned for low friction layers or coatings, other materials such as silicone and hydrophilic substances can be used instead of polytetrafluoroethylene if desired. Arched section 220 is made stiff enough to provide backup support for piercing the coronary artery wall as described below, as well as stability of the catheter in the coronary artery. Proximal sections of catheter 200 are constructed to provide appropriate pushability and trackability of the catheter along guide wire 100. For example, catheter 200 may have differing flexibility at different locations along its length.

As an alternative to having a medial portion 220 of catheter 200 arch as shown in FIGS. 4 and 5 when guide wire 100 is withdrawn from the catheter, a distal portion 220' of the catheter may be configured to deflect or curve to the side when guide wire 100 is withdrawn as shown in FIG. 5a. Catheter 200 in FIG. 5a is positioned in coronary artery 20 so that after portion 220' curves to the side, the distal end of lumen 210 points to a location on the inside of the side wall of the artery similar to the location of the apex of the arch 220 in FIG. 5 (i.e., the location on the coronary artery side wall at which it is desired for a piercing structure exiting from the distal end of lumen 210 to pierce the side wall of the coronary artery as referred to above and as described in more detail below). Thus in the embodiment shown in FIG. 5a, lumen 210 does not need a separate, additional side exit 210a for the piercing structure because the distal end of lumen 210 can be used as the exit for the piercing structure. In other respects embodiments of the type shown in FIG. 5a can be constructed and operated similarly to embodiments of the type shown in FIG. 5 and described above. The deflection of portion 220' is preferably such that after deflection one side of catheter 200 bears on the inside of one side of the coronary artery side wall at location 20d in order to maintain the distal end of the catheter close to or in contact with the other side of the coronary artery side wall at axially spaced location 20e. Further depiction and explanation of the invention will be made with reference to embodiments of the FIG. 5 type, but it will be understood that embodiments of the FIG. 5a type can be used instead if desired.

While it is not necessary to perform the above-described coronary artery access steps of the invention first, it may be preferable to do so to make sure that catheter 200 can be passed through occlusion 22 before committing to the other steps that will now be described.

Figure 7:
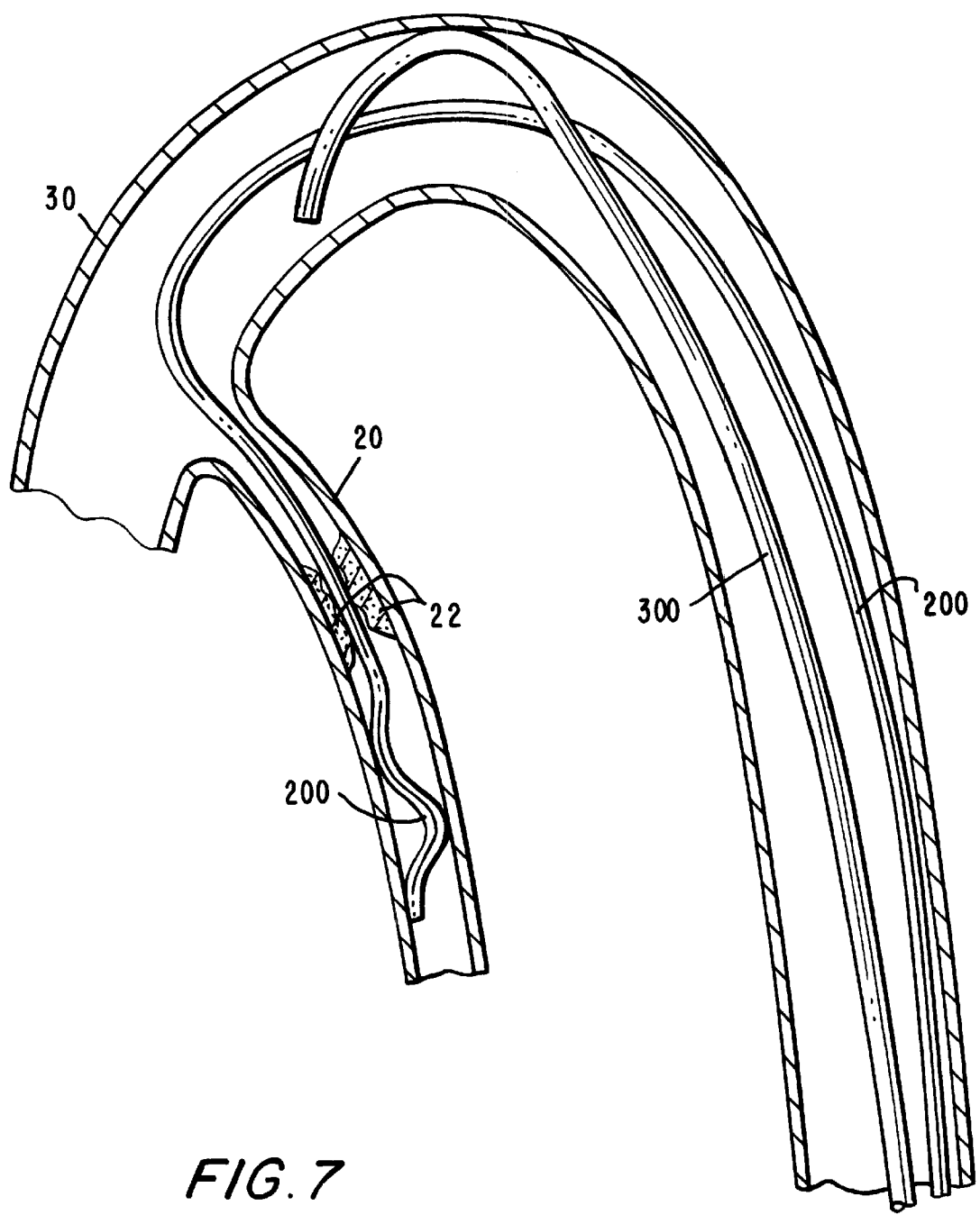
FIG. 7 is another view similar to FIG. 4 showing an even later stage in use of illustrative apparatus and methods in accordance with the invention.

A further step in accordance with the invention relates to accessing the aortic end of the desired bypass around occlusion 22. (See also Berg et al. U.S. patent application Ser. No. 09/014,759, filed Jan. 28, 1998 and hereby incorporated by reference herein in its entirety, for additional and/or alternative apparatus and/or methods usable in the aortic access that will now be described.) Another catheter or catheter-like structure 300 is introduced intraluminally into the aorta as shown in FIG. 7. Like guide wire 100 and catheter 200, catheter 300 is preferably introduced into the patient at a location emote from the coronary area. For example, catheter 300 may be introduced into the patient via a femoral artery. Also like guide wire 100 and catheter 200, the distal portions of catheter 300 are preferably remotely controlled from proximal portions of the apparatus which remain outside the patient at all times.

Figure 8:
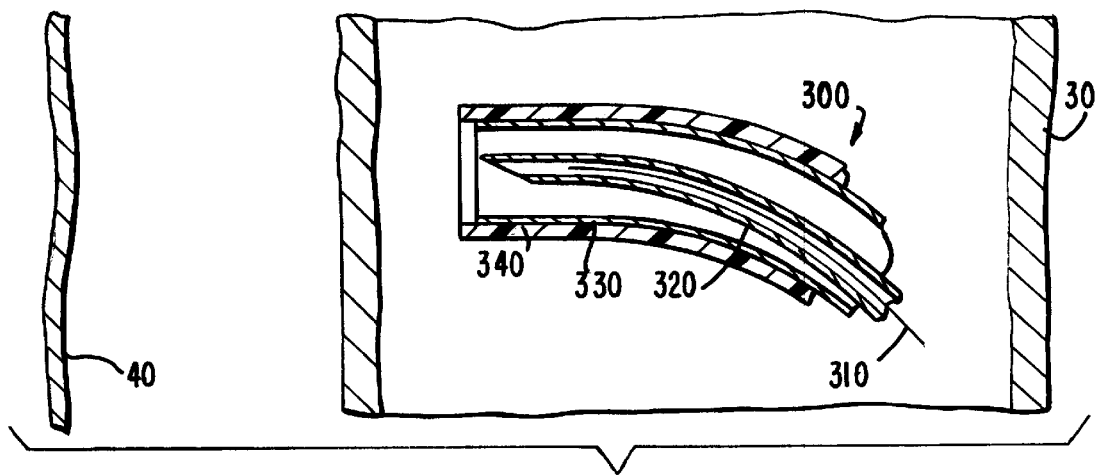
FIG. 8 is a simplified enlargement of a portion of FIG. 7, but with additional parts shown in section.

A preferred construction of catheter 300 is shown in more detail in FIG. 8. (See also Berg et al. U.S. patent application Ser. No. 09/010,367, filed Jan. 21, 1998 and hereby incorporated by reference herein in its entirety, for possible additional and/or alternative features for catheter 300.) There it will be seen that catheter 300 preferably includes pilot wire 310 disposed substantially concentrically inside hollow tubular needle catheter 320. Needle catheter 320 is disposed substantially concentrically inside hollow tubular cutter catheter 330, which in turn is disposed substantially concentrically inside hollow tubular aortic access catheter 340.

Catheter 300 is pushed into the patient until its distal portion is adjacent the inside surface of the wall of the aorta where it is desired to connect the aortic end of the bypass graft around occlusion 22 (see FIGS. 7 and 8).

Figure 9:
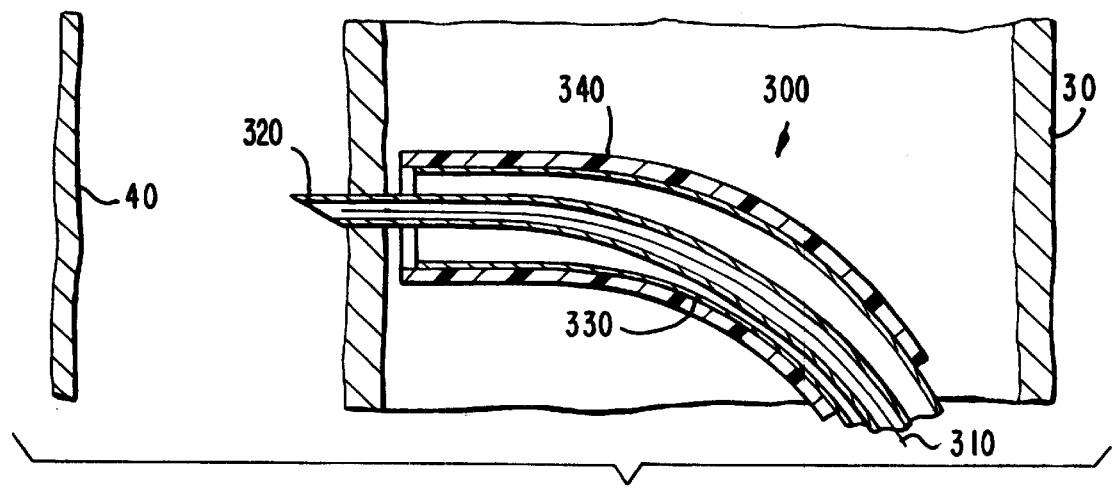
FIG. 9 is another view similar to FIG. 8 showing a later stage in use of illustrative apparatus and methods in accordance with the invention.

Needle catheter 320 is then pushed distally so that its sharpened distal end portion passes through the wall of aorta 30 as shown in FIG. 9. Note that, as FIG. 9 shows, needle catheter 320 preferably does not reach the pericardial membrane 40. The distal portion of needle catheter 320 may be barbed as shown at 322 in FIG. 9a to help prevent the needle catheter from being inadvertently pulled back through the wall of aorta 30 and for other purposes that will be mentioned below.

Figure 10:
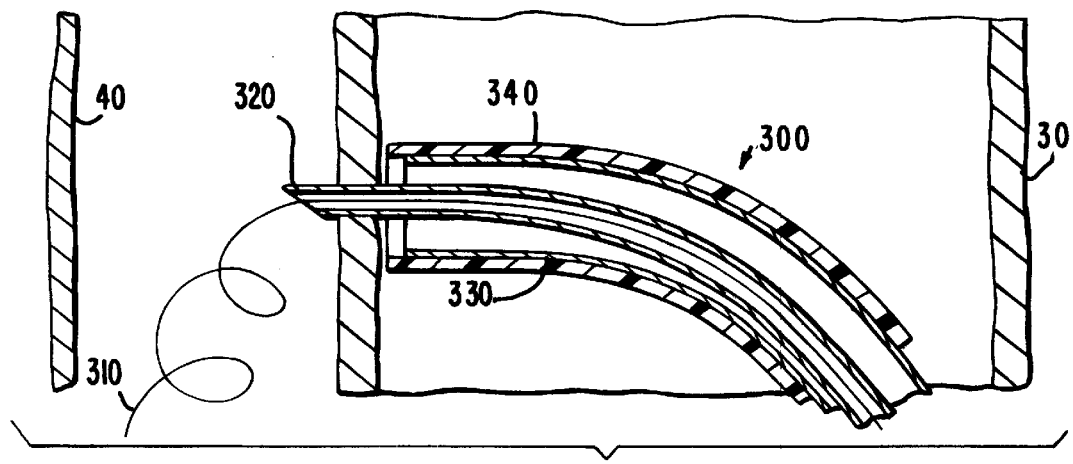
FIG. 10 is another view similar to FIG. 9 showing a still later stage in use of illustrative apparatus and methods in accordance with the invention.

The next step is to push the distal portion of pilot wire 310 out of the distal end of needle catheter 320 and into the space between aorta 30 and pericardial membrane 40 as shown in FIG. 10. Wire 310 is preferably too flexible where not supported by needle catheter 320 to pierce pericardial membrane 40. A quantity of wire 310 therefore deposits itself in the space between aorta 30 and membrane 40 as shown in FIG. 10.

Figure 9A:
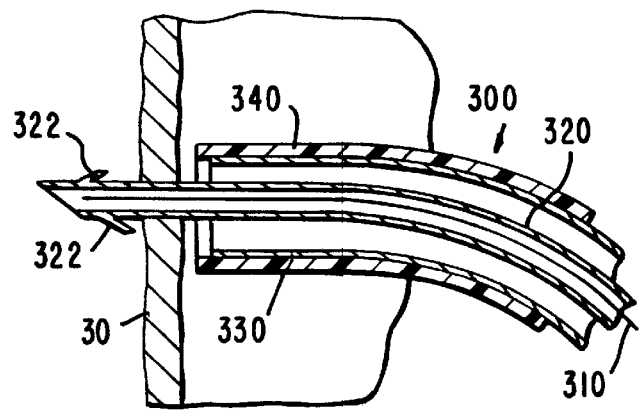
FIG. 9a is another view similar to FIG. 9 showing an alternative embodiment in accordance with the invention.
Figure 11:
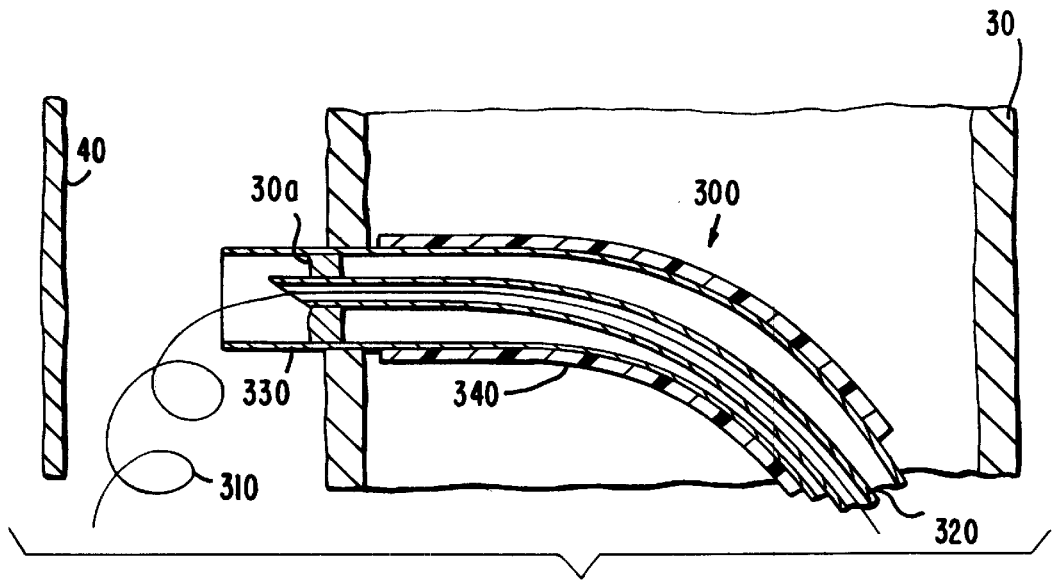
FIG. 11 is another view similar to FIG. 10 showing an even later stage in use of illustrative apparatus and methods in accordance with the invention.

The next step is to push cutter catheter 330 in the distal direction so that a sharpened distal end of catheter 330 makes an annular cut through the wall of aorta 30 as shown in FIG. 11. If provided as shown in FIG. 9a, barbs 322 on needle catheter 320 help hold the toroidal "doughnut" 30a of aorta wall tissue that is cut away by cutter catheter 330 on the distal portion of catheter 320. Cutter catheter 330 may be rotated about its central longitudinal axis to help it cut through the aorta wall tissue. After passing through the aorta wall as shown in FIG. 11, the distal portion of cutter catheter 330 tends to follow pilot wire 310 in the space between aorta 30 and pericardial membrane 40. This helps prevent cutter catheter 330 from inadvertently cutting through membrane 40. A typical diameter for cutter catheter 330 is approximately 3 mm. The cutter catheter shaft functions as a plug through the aperture in the aorta wall that the cutter catheter has formed. This prevents blood flow from the aorta into the pericardial space.

Figure 12:
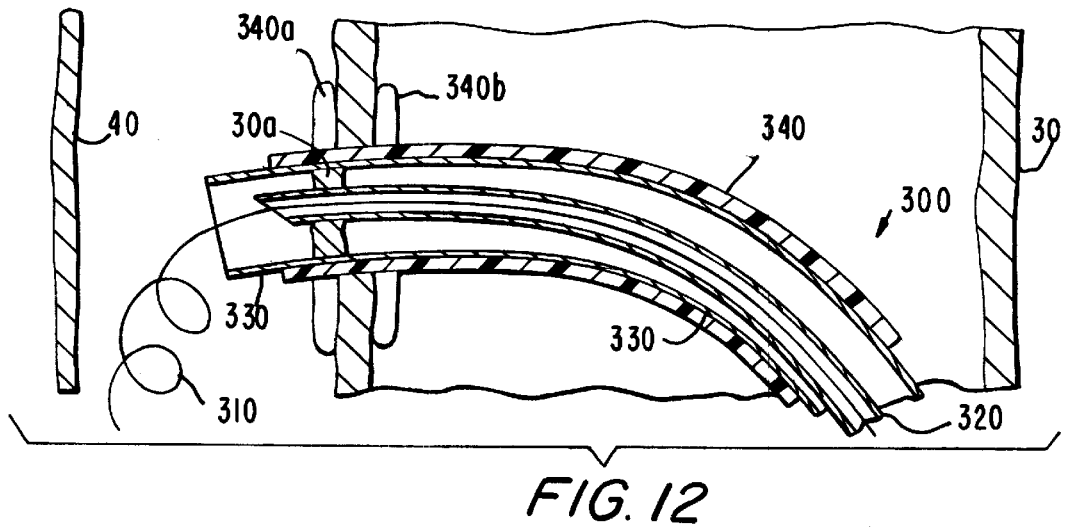
FIG. 12 is another view similar to FIG. 11 showing a still later stage in use of illustrative apparatus and methods in accordance with the invention.

The next step is to push the distal portion of aortic access catheter 340 through the aperture in the aorta wall that the cutter catheter has formed as shown in FIG. 12. To do this, aortic access catheter 340 uses the shaft of cutter catheter 330 as a guide. Assuming that the diameter of the cutter catheter is approximately 3 mm, the diameter of aortic access catheter 340 may be approximately 5 mm. The resulting expansion of the aortic opening from 3 mm to 5 mm makes use of the elastic recoil of the aorta to help seal the aortic opening around catheter 340, thereby ensuring no blood leakage into the pericardial space while catheter 340 is positioned through the aorta wall. The outer surface of catheter 340 may be coated with a hydrophilic material to facilitate advancement through the aorta wall. If the aorta wall does not provide sufficient elastic recoil, selectively inflatable annular sealing balloons 340a and/or 340b can be added to catheter 340 to provide sealing (see, for example, Berg et al. U.S. patent application Ser. No. 09/010,367, filed Jan. 21, 1998, which is hereby incorporated by reference herein in its entirety). When inflated, balloons 340a and 340b bear resiliently on the respective inner and outer surfaces of the aorta wall annularly around the aperture through that wall. Balloons 340a and/or 340b may also be desirable to help anchor the distal end of catheter 340 through the aperture in the aorta wall. In particular, balloon 340a (which is only inflated after catheter 340 has been pushed through the aorta wall aperture) helps prevent catheter 340 from being inadvertently pulled back out of the aorta wall aperture. Balloon 340b helps prevent catheter 340 from being pushed too far through the aorta wall aperture.

Figure 13:
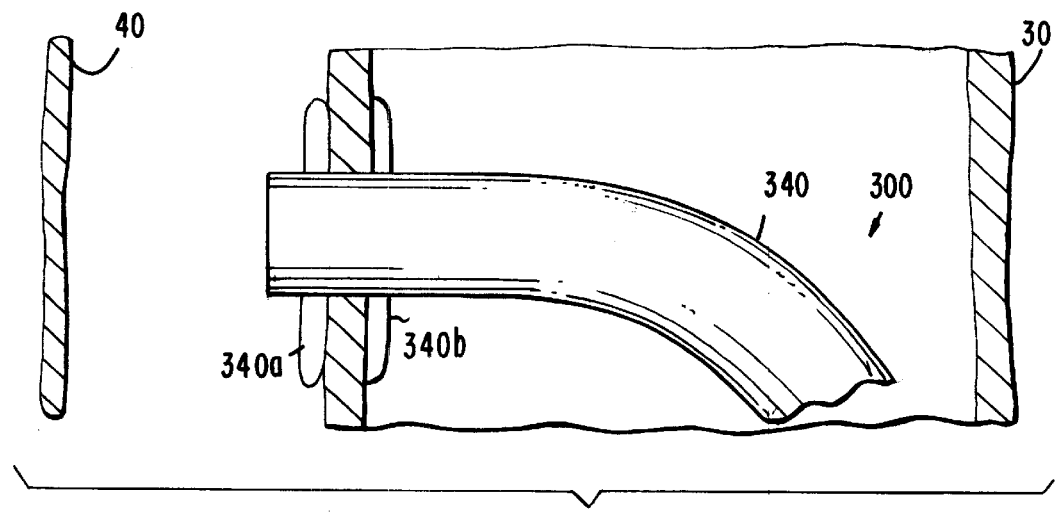
FIG. 13 is another view similar to FIG. 12 showing an even later stage in use of illustrative apparatus and methods in accordance with the invention.

The next step, shown in FIG. 13, is to pull all of components 310, 320, and 330 proximally out of catheter 340. The aorta wall tissue portion 30a cut away by cutter catheter 330 comes out of the patient with components 310, 320, and 330. Barbs 322 (FIG. 9a) on needle catheter 320 help ensure that tissue portion 30a is thus removed from the patient.

Figure 14:
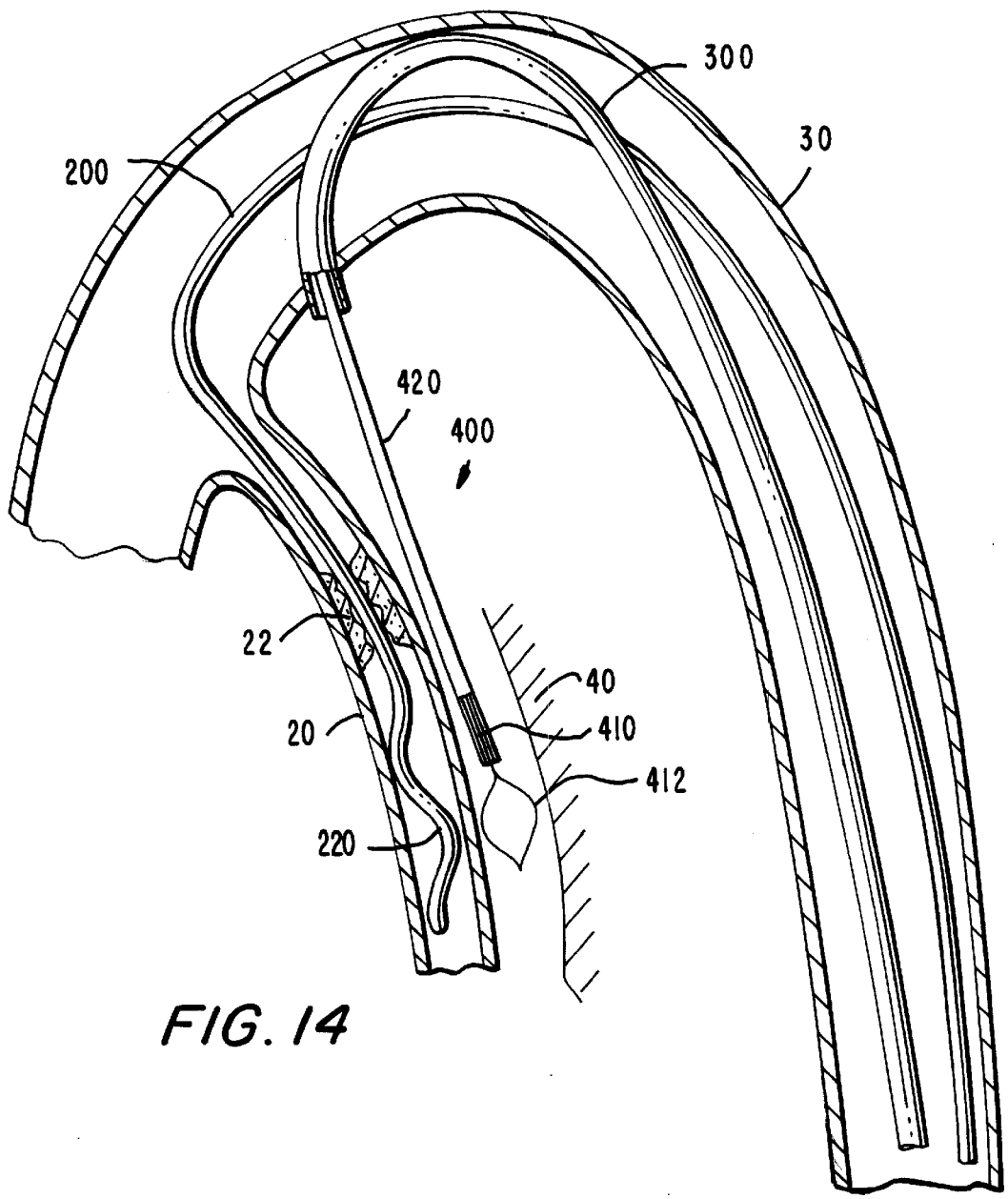
FIG. 14 is another view similar to FIG. 7 showing a still later stage in use of illustrative apparatus and methods in accordance with the invention.

A further step is shown in FIG. 14 and involves insertion of snare structure 400 axially through the lumen of aortic access catheter 300, starting from the proximal portion of the catheter, until a distal portion of structure 400 extends from the distal end of catheter 300 into the space between artery 20 and pericardial membrane 40. Structure 400 is preferably steerable (at least in its distal portion), and may include optical or video components to help the physician guide the distal portion of structure 400 to the vicinity of the distal portion 220 of catheter 200. The snare loop 412 on the distal end of wire 410 may not be extended from the surrounding snare sleeve 420 as shown in FIG. 14 until after the distal-most portion of sleeve 420 has reached the vicinity of catheter portion 220.

Although structure 400 may be constructed in other ways, particularly preferred constructions of some of the components of that structure are shown in FIGS. 15a–j. In FIGS. 15a–e horizontally aligned portions are superimposed on one another when these various components are assembled in structure 400. Component 510 includes stranded pull wire 512 securely attached at its distal end to metal bullet nose member 514. (In the assembled apparatus, member 514 forms the distal end of structure 400 (not including the possible further distal extension of snare loop 412 as shown in FIG. 14).) Component 520 includes hypotube portion 522 secured at its distal end to flat wire coil portion 524. Component 530 is a multilumen polymer tube. Portion 532 is preferably a relatively soft durometer polymer. Portions 534, 538, and 540 are preferably a relatively hard durometer polymer. Portion 536 is preferably an intermediate durometer polymer. Component 550 is a hollow tubular braid of high tensile strength wires configured to fit concentrically around the outside surface of portions 536 and 538 of component 530. For example, component 550 may be formed by braiding several wires tightly around the outer surface of the appropriate portions of component 530. Component 560 is a hollow polymer tube adapted to fit concentrically around the outside of component 550. For example, component 560 may be formed by extruding suitable polymer material around the outside of component 550 on component 530 so that the material of component 560 bonds to component 530 through interstices in component 550. Portion 562 is preferably an intermediate durometer polymer (e.g., like portion 536). Portion 564 is preferably a relatively hard durometer polymer (e.g., like portions 534, 538, and 540).

Figure 15A:
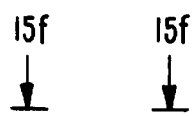
Figure 15B:
Figure 15C:
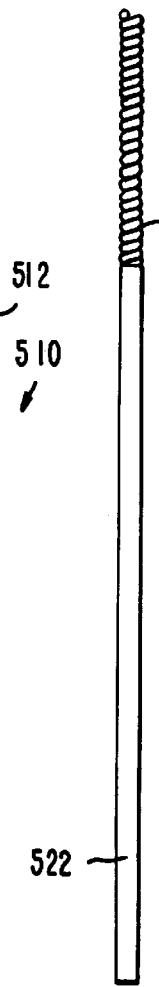
Figure 15D:
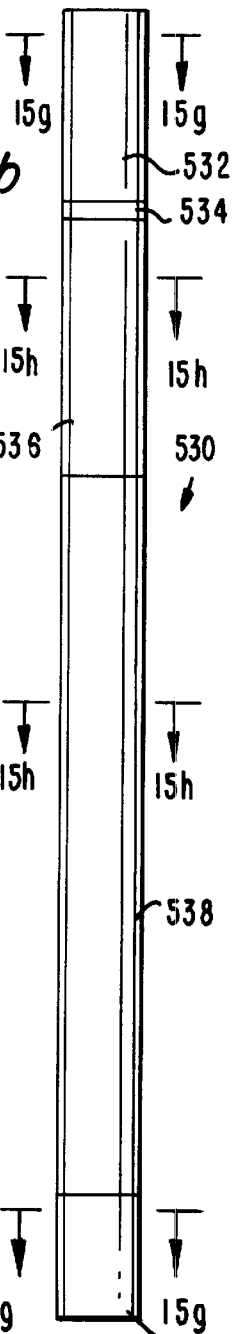
Figure 15E:
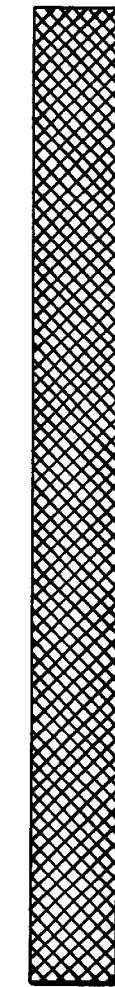
Figure 15F:
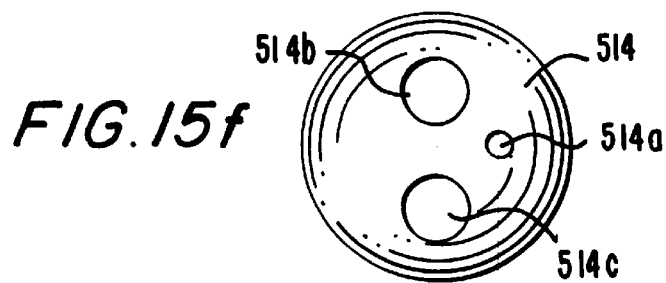
Figure 15G:
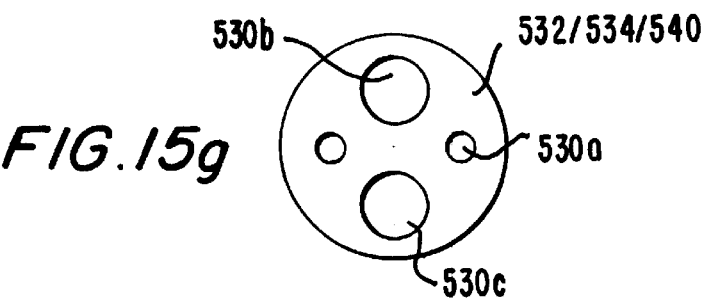
FIG. 15g is a simplified sectional view taken alone either of the lines 15g—15g in FIG. 15c.
Figure 15H:
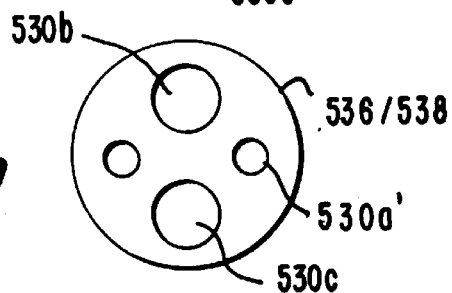
FIG. 15h is a simplified sectional view taken along either of the lines 15h—15h in FIG. 15c.
Figure 15I:
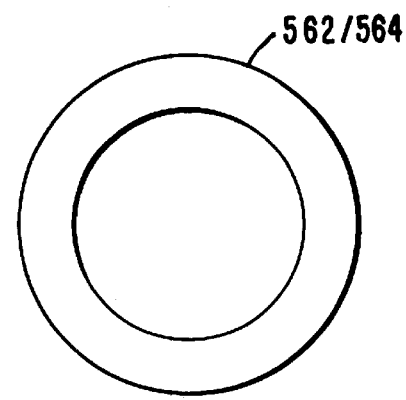
FIG. 15i is a simplified sectional view taken along either of the lines 15i—15i in FIG. 15e.

As can be seen in FIG. 15f, bullet nose 514 has a relatively small axial bore 514a for receiving and attaching the distal end of pull wire 512. Bullet nose 514 also has two relatively large bores 514b and 514c. In the assembled structure, bore 514a is axially aligned with lumen 530a/530a' (or the similar diametrically opposite lumen) in component 530 (see FIGS. 15g and 15h). Similarly, in the assembled structure, bores 514b and 514c are aligned with lumens 530b and 530c in component 530.

Component 530, initially without portion 540, may be formed on several mandrels, each of which is subsequently pulled out the proximal end of component 530 to leave a respective one of the lumens in that component. Component 520 may then be inserted into lumen 530a' from the proximal end of component 530. Component 510 may then be added from the distal end of component 530 so that pull wire 512 passes through lumen 530a and component 520. Portion 540 may then be attached as shown in more detail in FIG. 15j.

Figure 15K:
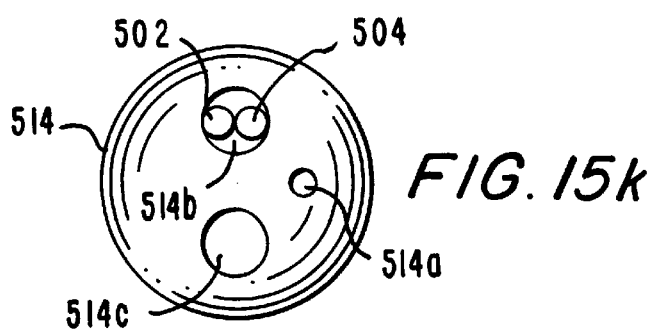
FIG. 15k is another view similar to FIG. 15f showing the possible inclusion of additional components in accordance with the invention.
Figure 15J:
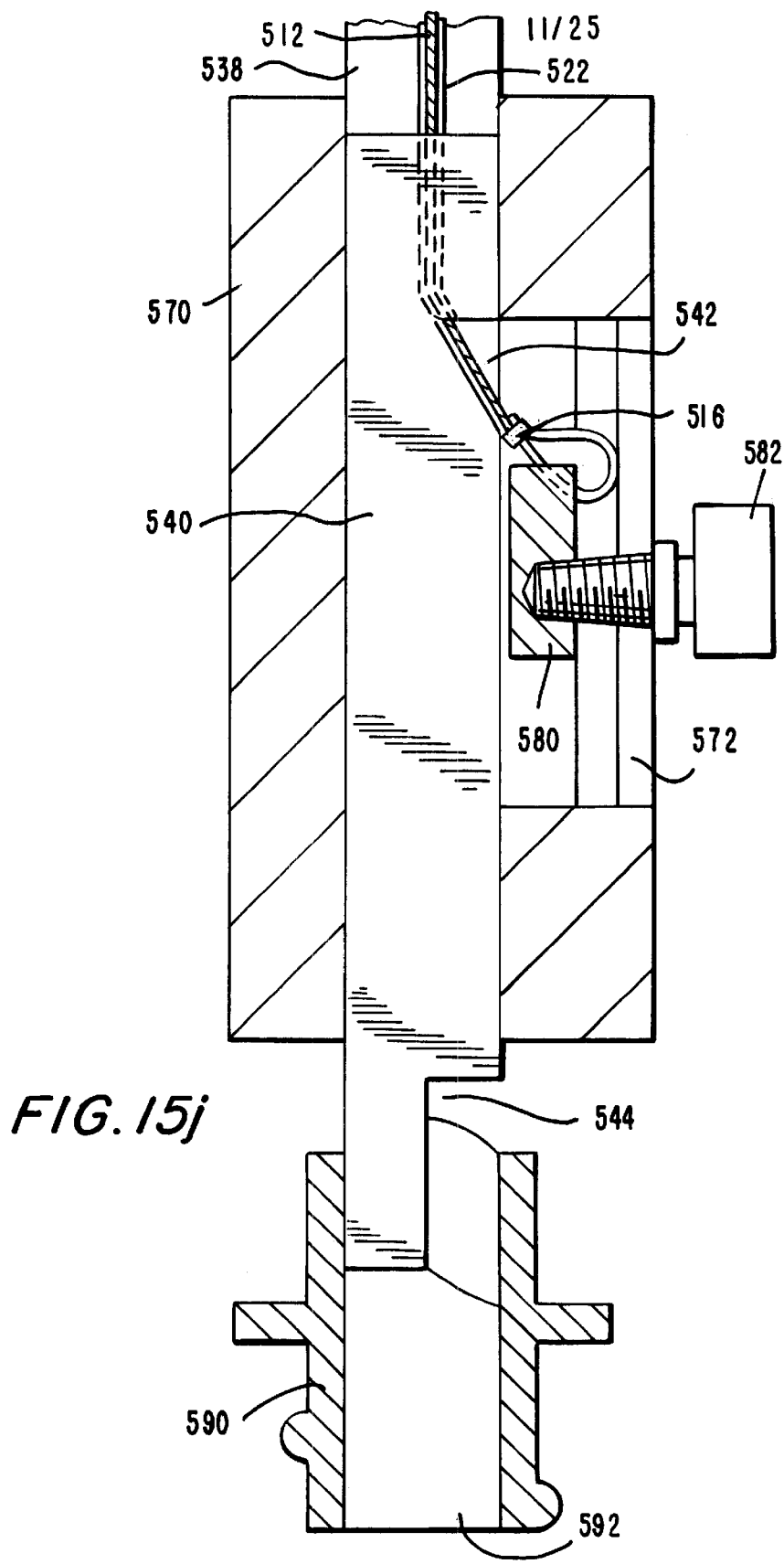
FIG. 15j is a simplified view, partly in section, of additional components of an illustrative embodiment of a portion of the apparatus shown in FIG. 14.

An Illustrative proximal handle and control portion of structure 400 is shown in FIG. 15j. An enlarged handle member 570 is secured around portion 540 of component 530. Handle member 570 has an axial slot 572 in which slide block 580 is captive in the radial direction of member 570 but slidable in the axial direction of member 570. A thumb screw 582 is threaded into block 580 to act as a handle for sliding block 580 axially relative to member 570 when the thumb screw is sufficiently loosely threaded into block 580, and to act as a releasable lock for locking block 580 in any desired axial position along slot 572 when thumb screw 582 is threaded more tightly into block 580 and therefore against the outer surface of handle member 570.

A side region of portion 540 is notched at 542 to allow the proximal portion of pull wire 512 to come out of the side of portion 540 for looping through block 580. The loop in pull wire 512 is fixed by a crimp 516 around the wire at the base of the loop. Accordingly wire 512 can be pulled proximally by various amounts relative to the remainder of structure 400 by sliding block 580 proximally relative to handle member 570. Pulling wire 512 proximally causes the relatively soft distal portion 532 of component 530 to curve in the direction of the side of component 530 that wire 512 is closest to. Relaxing are 512 allows portion 532 to straighten out again. The above-described curving is largely confined to distal portion 532 because that portion is made of the softest material and because component 520 substantially reduces any tendency of other axial portions of the apparatus to curve in response to tension in wire 512. All axial portions of structure 400 are, however, sufficiently flexible to pass along the patient's tubular body structure through aortic access catheter 300.

Component 550 helps structure 400 transmit torque from its proximal handle 570 to its distal end. The physician can use the combination of such torque and the ability to curve the distal portion 532 of structure 400 to maneuver the distal portion of that structure from the distal end of catheter 300 to a location adjacent catheter portion 220, all preferably inside pericardial membrane 400. Radiologic markers may be provided on structure 400 to help the physician determine when the distal portion of that structure is properly located. One (or more) of the lumens through component 530 (and bullet nose 514) may be used to enable structure 400 to also function as an endoscope to aide in maneuvering the distal portion of structure 400 adjacent to catheter portion 220. As shown in FIG. 15k, for example, optical fibers 502 extending along a lumen of component 530 may be used to convey light from outside the patient to illuminate the interior of the patient just beyond bullet nose 514. Other parallel optical fibers 504 may be used to convey the resulting illuminated scene back to an eyepiece or other optical or video viewing apparatus outside the patient.

A luer 590 may be attached to the proximal end of portion 540 as shown in FIG. 15j, if desired, so that the luer conduit 592 communicates with one (or more) of the lumens through components 530 (and bullet nose 514). This may provide the passage via which the above-mentioned optical fibers 502/504 exit from the remainder of the apparatus. It may also form a passageway for introducing fluids into or draining fluids from the patient adjacent bullet nose 514.

Another of the lumens through component 530 (and bullet nose 514) is opened outside the patient via the notch 544 (FIG. 15j) in a proximal part of portion 540. Notch 544 provides the entrance point for snare loop 412 and wire 410. The portion of structure 400 around this lumen therefore forms what is referred to as the snare sleeve 420 in the earlier discussion of FIG. 14.

It will be understood that any number of passageways like 514b–c/530b–c can be provided through elements 514 and 530.

Components 410 and 412 can take any of many forms, some alternatives being specifically illustrated and described later in this specification. For present purposes, however, it will be sufficient to assume that component 412 is a loop of wire which is secured to the distal end of wire 410 and which is resiliently biased to spring open when extended distally from the distal end of a lumen in sleeve 420 as shown in FIG. 14. Also as shown in FIG. 14, the distal portion of sleeve 420 is preferably positioned in the patient so that when loop 412 is extended distally from sleeve 420, loop 412 will receive a pierce structure passed out of coronary artery 20 via catheter portion 220 as will now be described.

Figure 16:
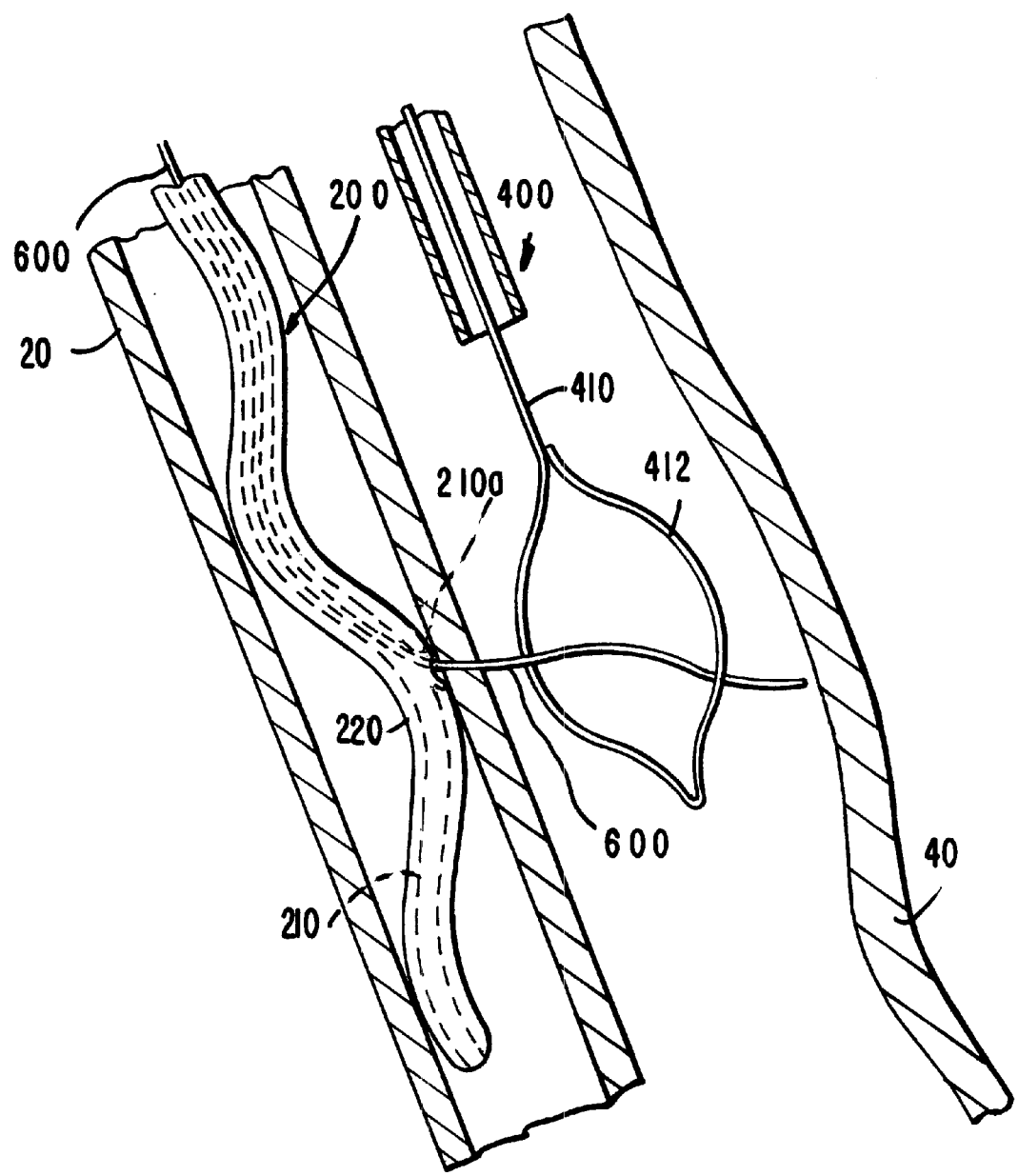
FIG. 16 is a simplified view similar to a portion of FIG. 14 showing a later stage in use of illustrative apparatus and methods in accordance with the invention.

A further step is illustrated by FIG. 16 and involves inserting an elongated piercing structure 600 (e.g., primarily a metal wire or wire-like structure) into catheter 200 along the lumen 210 formerly used for guide wire 100. Because catheter portion 220 is now arched as shown in FIG. 16, the distal end of piercing structure 600 tends to follow lumen branch 210a out of catheter 200 and into contact with the interior surface of the side wall of coronary artery 20. The distal tip of piercing structure 600 is sufficiently sharp and structure 600 is sufficiently stiff that the distal tip of structure 600 can be pushed out through the coronary artery wall tissue (see also FIG. 17). Continued distal pushing of structure causes the portion outside coronary artery 20 to pass through snare loop 412. The distal portion of piercing structure 600 is, however, preferably not strong enough, when outside coronary artery 20 and therefore unsupported by catheter lumen 210, to pierce or otherwise damage pericardial membrane 40. The main component of structure 600 may be metal (e.g., nitinol) wire. Radiologically visible marker bands 610 may be provided on the distal portion of piercing structure 600 to help the physician monitor the progress and position of that portion of structure 600. Alternatively, structure 600 may be made of a radiologic (e.g., radio-opaque) material such as tungsten wire.

Figure 18:
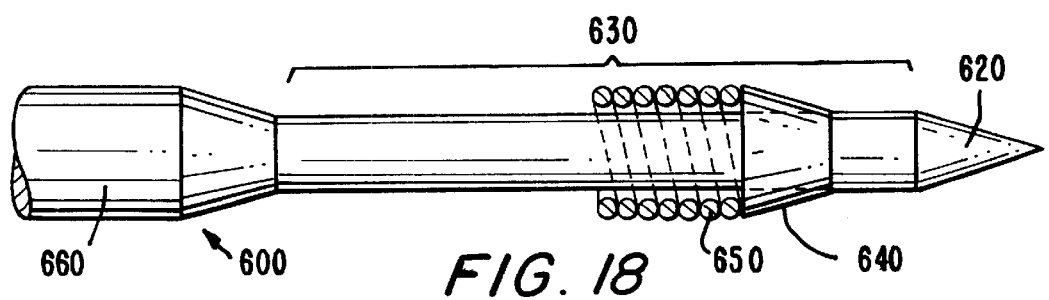
FIG. 18 is a simplified elevational view, partly in section, of an illustrative embodiment of a portion of the apparatus shown, for example, in FIG. 17 in accordance with the invention.

An illustrative construction of the distal portion of structure 600 is shown in more detail in FIG. 18. There it will be seen that this part of structure 600 has a sharpened distal tip portion 620, which may be approximately 0.1 inches in length. Behind the distal tip is a relatively slender elongated portion 630. For example, portion 630 may have a diameter of approximately 0.006 inches and a length of approximately 1.575 inches. A hollow frusto-conical dilator 640 may be provided a short distance in from the distal end of portion 630. Just proximal of dilator 640 portion 630 may be wound with a radiologically viewable wire 650. For example, wire 650 may be gold or platinum wire. Dilator 640 helps provide a gradual transition from the smaller diameter of portion 630 distal of wire 650 to the larger diameter produced by the addition of coil 650. Proximal of portion 630 structure 600 transitions gradually to relatively large diameter portion 660. For example, the diameter of portion 660 may be approximately 0.01 inches.

Distal portions 620 and 630 are stiff enough, when supported by lumen 210, to pierce the wall of coronary artery 20. At a greater distance from the support of lumen 210, however, portions 620 and 630 are preferably not stiff enough to pierce or otherwise damage pericardial membrane 40. In addition, distal portions 620 and 630 are not stiff enough to straighten out arched catheter portion 220 when portions 620 and 630 are inside catheter portion 220. The relatively slender distal portions 620 and 630 of structure 600 engage and pierce the wall of coronary artery 20 before the larger proximal portion 660 enters the curved portion 220 of catheter 200. Proximal portion 660 is made somewhat larger and therefore stiffer to help transmit the pushing force required to enable distal portions 620 and 630 to pierce the coronary artery wall.

Figure 19A:
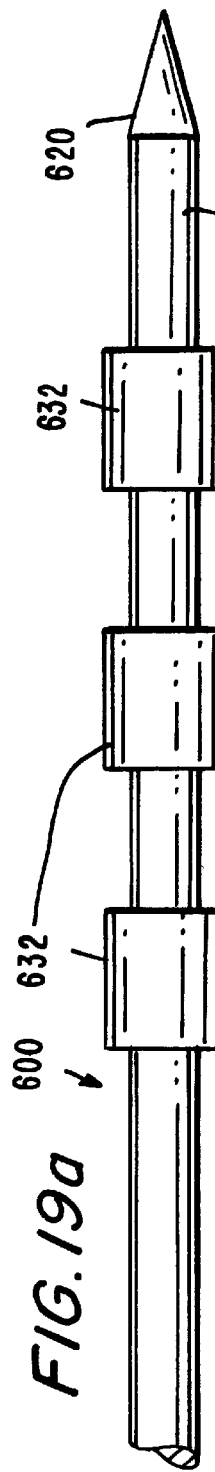
FIG. 19a is a simplified elevational view of a component of another illustrative embodiment of a portion of the apparatus shown, for example, in FIG. 17 in accordance with the invention.
Figure 19B:
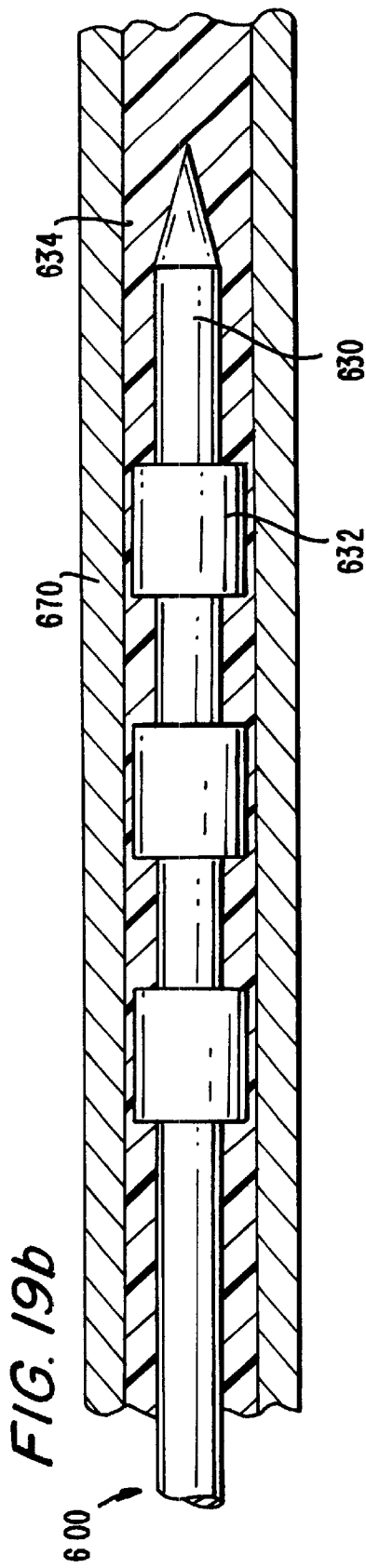
FIG. 19b is a simplified elevational view, partly in section, showing an intermediate stage in processing the component of FIG. 19a in accordance with the invention.
Figure 19C:
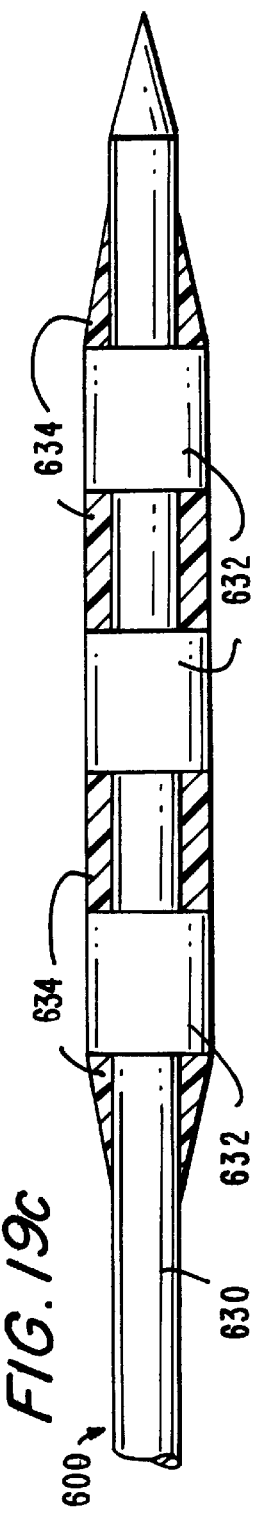
FIG. 19c is a simplified elevational view, partly in section, showing a final condition of the component of FIG. 19a in accordance with the invention.

Another illustrative way to provide marker bands 610 on piercing structure 600 is shown in FIGS. 19a–c. In this embodiment the distal portion 630 of structure 600 is provided with several diametrically enlarged portions 632 axially spaced along portion 630. The distal portion of structure 600 is inserted into the lumen of a heat shrinkable tube 670 which initially has an inner diameter which is slightly greater than the outer diameter of enlarged portions 632. A radiologically viewable adhesive 634 is then injected into tube 670 so that the adhesive flows around the outside of distal portion 630. Tube 670 is then heat shrunk to more closely conform to the outer diameter of portion 630, and adhesive 634 is then cured. Tube 670 is then removed, and the extreme proximal and distal regions of adhesive 634 are tapered down to the diameter of portion 630. The resulting bands of adhesive 634 adjacent to or between portions 632 provide radiologically viewable markers 610 on structure 600.

A highly desirable feature of structure 600 no matter how it is constructed (e.g., as in FIG. 18, FIGS. 19a–c, or in any other way) is that it has a substantially transitionless external profile to ensure continual passage through the arterial wall. Any slight edges may snag on the artery wall and prevent structure 600 from exiting the coronary artery. Thus radio-opacity (e.g., 610, 634, 650) is preferably provided in structure 600 without adding abrupt transitions. Such radio-opacity allows efficient snaring of the distal end of structure 600 inside the pericardial sac. Radio-opaque markers 610 can be plated, bands, or coils. Suitable marker materials include gold, tungsten, and platinum. Radio-opaque markers having predetermined spacing may also be provided along the length of structure 600 to make it possible to use structure 600 to measure the length of graft needed between aorta 30 and coronary artery 20. This possible use of radiologic markers on structure 600 will become clearer as the description proceeds. The basic material of structure 600 is preferably super-elastic nickel titanium (nitinol), but other possible materials include stainless steel, tantalum, and suitable polymers.

As has been mentioned, structure 600 may be made of a radiologically viewable material such as tungsten to eliminate the need for the above-described radiologic markers 610/650/634.

FIGS. 20a and 20b illustrate a feature that piercing structure 600 may be provided with to help ensure that the piercing structure does not inadvertently pierce pericardial membrane 40 after exiting from artery 20. A distal portion of piercing structure 600 may be resiliently biased to deform into a serpentine shape 680 when it is no longer constrained to remain substantially straight by being inside catheter lumen 210. Thus, as the distal portion of piercing structure 600 exits from coronary artery 20 as shown in FIG. 20b, it takes on the above-described serpentine shape. When thus shaped, it is practically impossible to push the distal portion of piercing structure 600 through pericardial membrane 40. The serpentine shape of the distal portion of piercing structure 600 also helps ensure that at least some of that structure stands off outside coronary artery 20, thereby facilitating snaring of that portion of structure 600 by snare loop 412.

Another possible construction of the distal portion of structure 600 is shown illustratively in FIGS. 21a–c. In this embodiment an axially medial portion of structure 600 close to the sharpened distal top is cut through axially as indicated at 690 in FIG. 21a. In addition, the two lateral halves of the cut portion of structure 600 may be resiliently biased to spring apart as shown in FIG. 21b when unconstrained by lumen 210. While in lumen 210, the two lateral halves of cut structure 600 remain together, and with the support of lumen 210 the structure has sufficient column stiffness to pierce the wall of artery 20. Shortly after emerging from artery 20, however, the two lateral halves of structure 600 can separate as shown in FIG. 21c, and structure 600 loses its ability to pierce any further tissue such as pericardial membrane 40. The loop 692 that forms in the distal-most portion of structure 600 outside artery 20 provides an alternative means by which snare structure 400 can engage structure 600. In particular, a hook 412a can be used to hook onto loop 692 as shown in FIG. 21c.

As an alternative or addition to snaring the distal portion of piercing structure 600 with a snare loop 412 or hook 412a, other technologies may be used to make or help make a connection between structures 410 and 600. For example, the distal portion of structure 600 may be or may include a ferromagnetic material, and structure 410 may include a distal magnet for attracting and holding that ferromagnetic material. As another example, the distal portion of structure 410 may include a pliers-like gripper for closing on and gripping the distal portion of structure 600. As an alternative or addition to using fiber optics or the like in structure 400 to allow what might be called direct visual observation of the snaring of structure 600 by structure 410, both of these structures may be made of radiologic materials such as tungsten to permit radiologic observation of the snaring maneuvers.

Figure 22:
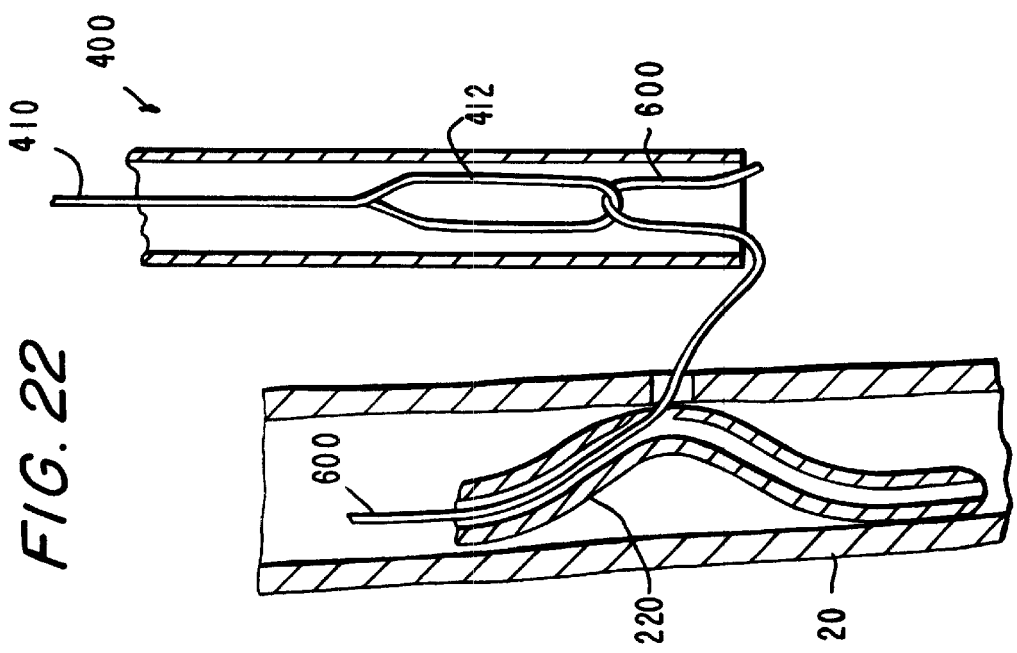
FIG. 22 is another view similar to FIG. 17 showing a later stage in use of illustrative apparatus and methods in accordance with the invention.

After a suitable connection or interengagement has been established between structures 410 and 600, a further step includes pulling structure 410 back proximally in order to pull structure 600 into structure 400. (In cases in which structure 600 is snared by a loop 412, the immediately above-mentioned step may be preceded by operating or manipulating structure 400 to close loop 412 on structure 600, and preferably also to deflect structure 600 around a portion of loop 412. For example, FIG. 22 shows shifting structure 400 distally relative to loop 412 to cause the loop to close and to deform structure 600 into what is effectively a hook through the closed loop. This provides a very secure link between structures 410 and 600.)

Figure 23:
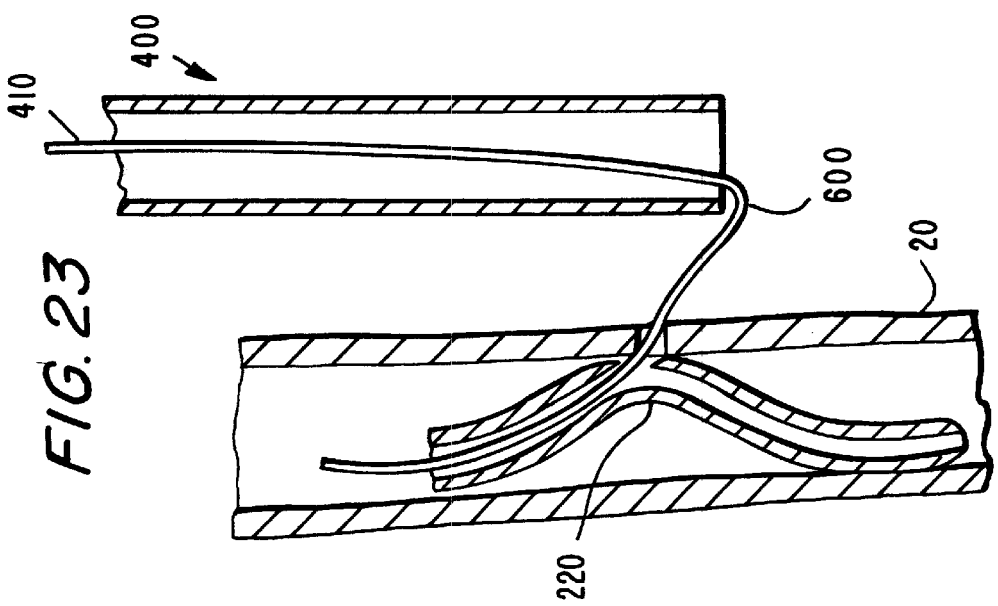
FIG. 23 is another view similar to FIG. 22 showing a still later stage in use of illustrative apparatus and methods in accordance with the invention.

As structure 410 is pulled back proximally relative to structure 400, structure 600 is pulled into structure 400. To help reduce the pulling stress on elements 410 and 600, additional length of structure 600 may be pushed into the patient at approximately the same rate that structure 410 is being pulled out of the patient. Eventually, structure 410 may be pulled completely out of the patient, and structure 600 may extend continuously through the patient from its initial entry point to the initial entry point of structure 410. The condition of the portions of the patient and apparatus shown in FIG. 22 may now be as shown in FIG. 23.

Figure 24:
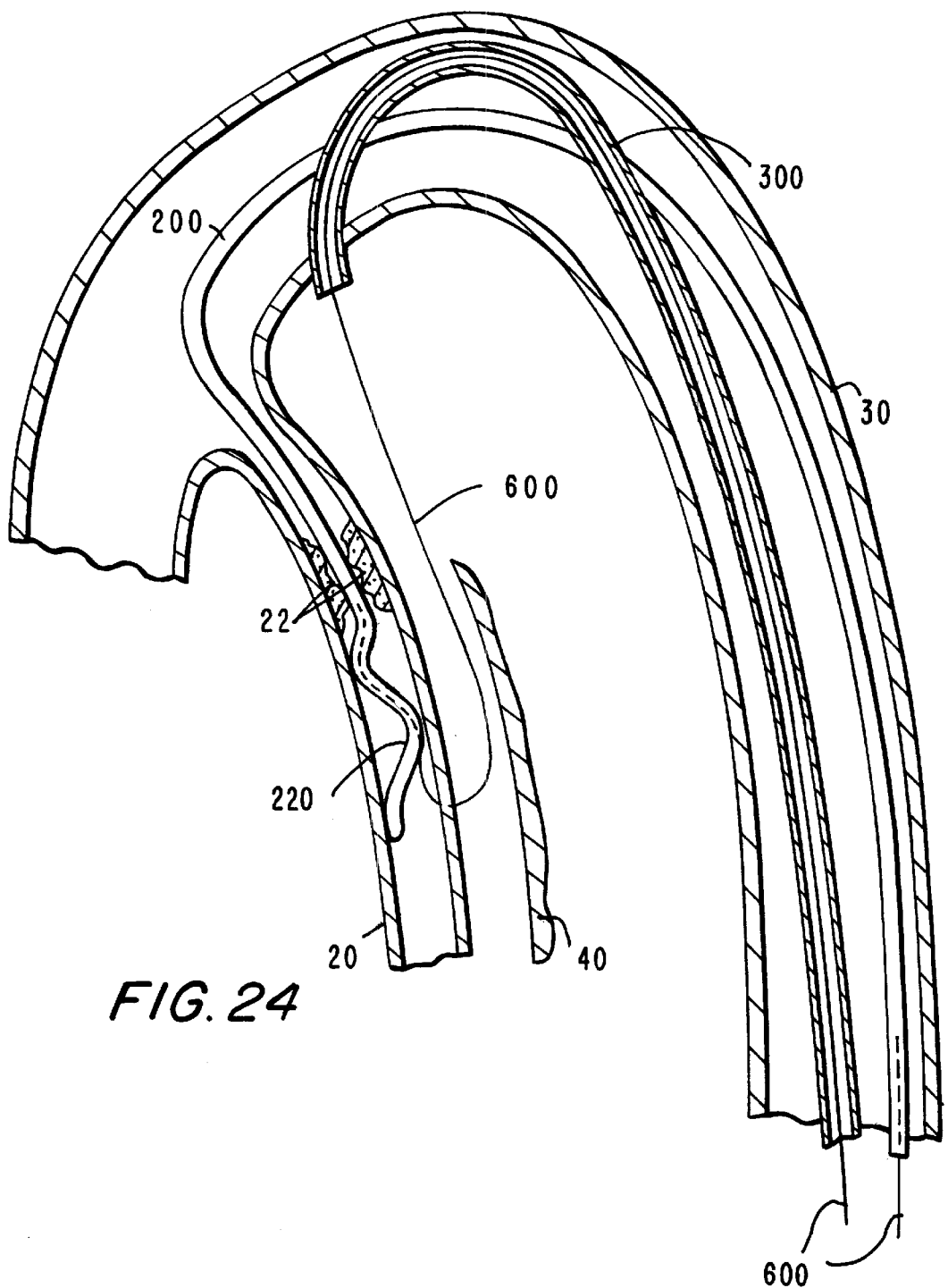
FIG. 24 is another view similar to FIG. 14 showing an even later stage in use of illustrative apparatus and methods in accordance with the invention.

A further step is to withdraw structure 400 from the patient. Structure 200 may also be withdrawn from the patient or is at least proximally retracted somewhat. The condition of the relevant portion of the patient and the apparatus after these operations may be as shown in FIG. 24. (FIG. 24 illustrates the case in which structure 200 is proximally retracted rather than being fully withdrawn from the patient at this stage.)

Figure 25:
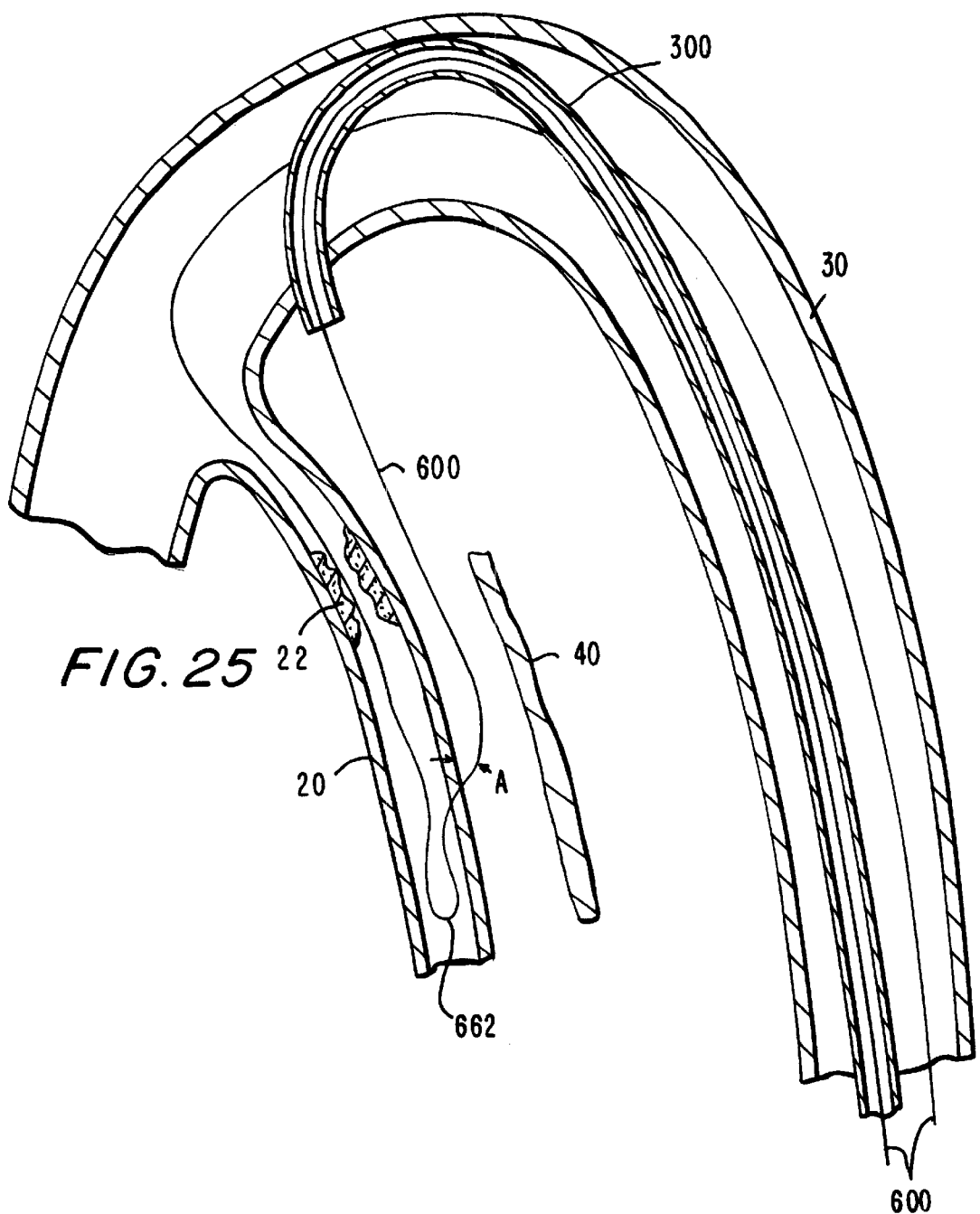
FIG. 25 is another view similar to FIG. 24 showing a possible additional feature of illustrative apparatus and methods in accordance with the invention.
Figure 26:
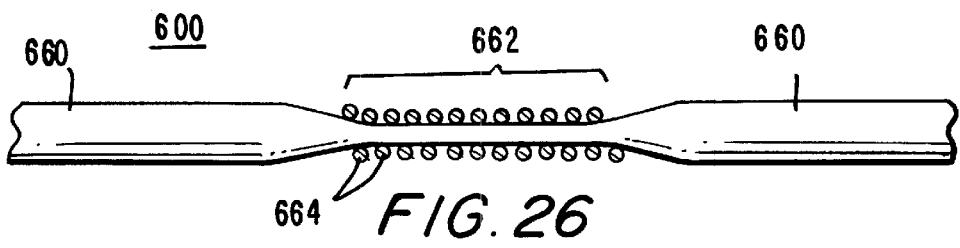
FIG. 26 is a simplified elevational view, partly in section, of an illustrative embodiment of a portion of the FIG. 25 apparatus in accordance with the invention.

To help provide a graft which connects to coronary artery 20 with an acute angle between the graft and the upstream portion of the coronary artery, it may be desirable to construct structure 600 so that a portion of that structure can be made to extend down into the downstream portion of the coronary artery beyond the point at which structure 600 passes through the side wall of the artery. An example of this type of structure 600 is shown in FIGS. 25 and 26. (FIG. 25 also illustrates a case in which structure 200 is completely withdrawn from the patient after structure 600 has been fully placed in the patient.)

For operation as shown in FIG. 25, structure 600 may be constructed as shown in FIG. 26 with an axially medial portion 662 having significantly greater flexibility than the axially adjacent portions of that structure. For example, structure 600 may have reduced diameter in region 662 to increase its flexibility in that area. Portion 662 may be provided with a radio-logic marker 664 (e.g., a wire of radio-opaque material wrapped around that portion of structure 600) to facilitate proper placement and other observation of portion 662 in the patient. Marker 664 preferably does not interfere with the increased flexibility of portion 662.

Continuing with the illustrative embodiment shown in FIGS. 25 and 26, after structure 600 has been established through the patient (e.g., as shown in FIG. 24), structure 600 is shifted axially in the patient until portion 662 is inside coronary artery 20 adjacent the point at which structure 600 passes through the side wall of the artery. This can be determined by radiologic observation of marker 664. Then both end portions of structure 600 can be pushed into the patient to cause structure 600 to essentially fold or prolapse at portion 662 and to push folded portion 662 down into the downstream portion of artery 20 as shown in FIG. 25. This causes the portion of structure 600 which is outside the upstream portion of artery 20 to form an acute angle A with the upstream artery portion. Such an acute angle A may be a preferable angle of approach for the bypass graft which is to be installed along structure 600 as described elsewhere in this specification.

Figure 27:
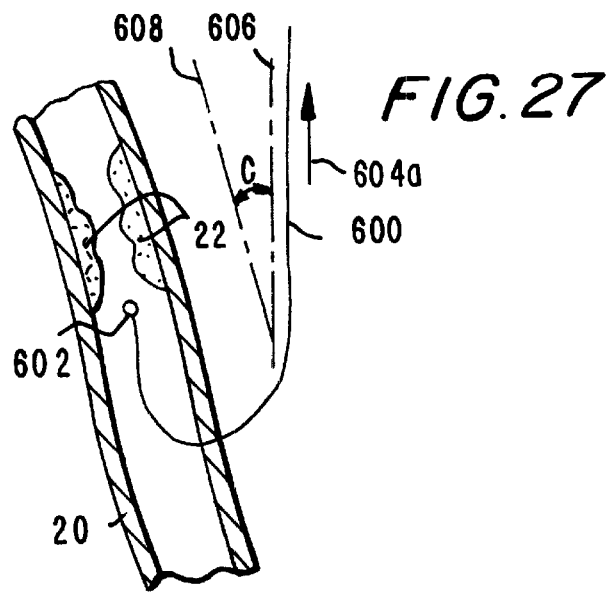
FIG. 27 is a view similar to a portion of FIG. 25 showing another illustrative embodiment of apparatus and methods in accordance with the invention.
Figure 28:
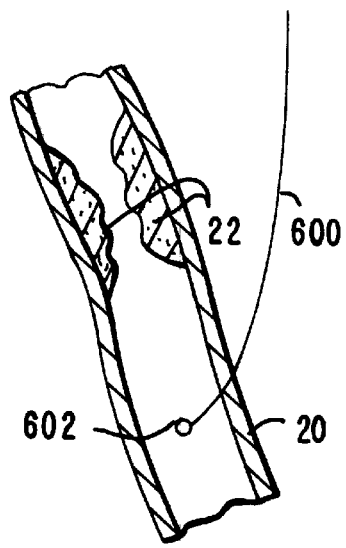
FIG. 28 is a view similar to FIG. 27 showing a later stage in use of the FIG. 27 apparatus.
Figure 29:
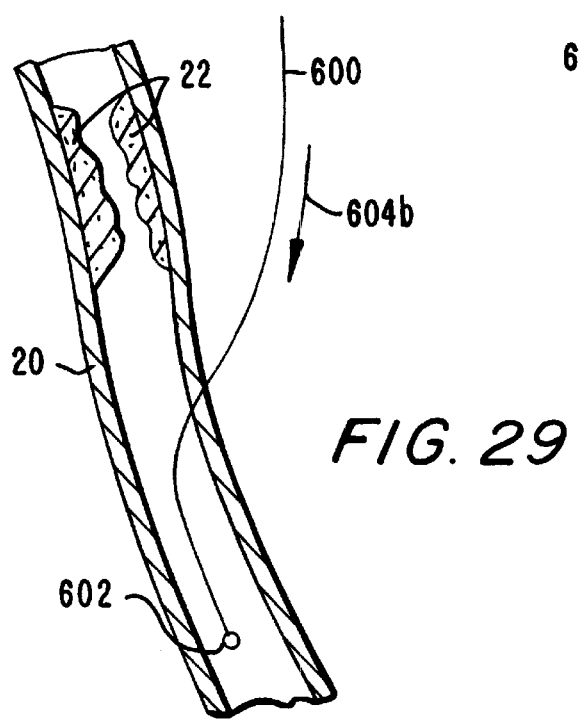
FIG. 29 is a view similar to FIG. 28 showing a still later stage in use of the FIG. 27 apparatus.

Another alternative (apparatus and method) for re-routing structure 600 in the patient (e.g., to achieve an acute angle approach of structure 600 to the outer surface of coronary artery 20) is shown in FIGS. 27–29. In this alternative the proximal end of the portion of structure 600 that extends up and out of the patient via coronary artery 20 is preferably provided with an atraumatic end 602. In the illustrative embodiment shown in FIGS. 27–29 atraumatic end 602 is a ball which covers what might otherwise be a relatively sharp end of structure 600. When it is desired to re-route structure 600 in the patient, structure 600 is pulled axially relative to the patient in the direction indicated by arrow 604a. This pulls atraumatic end 602 into the patient and ultimately into coronary artery 20 as shown first in FIG. 27 and then still farther as shown in FIG. 28.

When atraumatic end 602 reaches the condition shown in FIG. 28 where it is adjacent to the aperture in the side wall of coronary artery 20 through which structure 600 passes, the resilience of structure 600 (which, as has been said, may be a metal wire) causes what remains of structure 600 in the vicinity of the coronary artery side wall aperture to straighten. This causes the end 602 of structure 600 to move in the downstream direction along coronary artery 20 as shown in FIG. 28. The next step is to begin to push structure 600 back into the patient as shown by arrow 604b in FIG. 29. This causes end 602 to move in the downstream direction along the coronary artery lumen as is also shown in FIG. 29, thereby ultimately giving structure 600 a new routing immediately outside coronary artery 20 like the routing of the corresponding portion of structure 600 in FIG. 25.

It will be apparent from consideration of FIGS. 27–29 that at least the depicted portion of structure 600 is sufficiently laterally flexible to enable a distal part of that structure to extend inside the lumen in the upper portion of coronary artery 20, while a proximal part of structure 600 extends axially along a path 606 that is outside the upper portion of the coronary artery and that forms an acute angle C with a line 608 parallel to the upper portion of the artery. In other words, path 606 extends back along the outside of the upper portion of artery 20. At least the depicted portion of structure 600 is also sufficiently resilient so that when the part of structure 600 that remains in the lumen in the upper portion of coronary artery 20 becomes too short to continue to be constrained or guided by that artery portion, the part of structure 600 that remains in the artery switches resiliently into the lower portion of the artery as shown in FIG. 28. This switching happens automatically as a result of structure 600 resiliently tending to straighten when it is not otherwise deflected or constrained by its contact with the interior surfaces of artery 20. At least the depicted portion of structure 600 is also sufficiently laterally stiff that the distal part can be pushed down into the lower portion of artery 20 when the proximal part is pushed in the distal direction as indicated by arrow 604b in FIG. 29. In addition to providing an atraumatic end to structure 600, the fact that end 602 is radially enlarged relative to the axially adjacent portion of structure 600 helps prevent end 602 from being inadvertently pulled proximally out of artery 20 when the structure approaches the condition shown in FIG. 28 and before structure 600 begins to be pushed into the artery again as shown in FIG. 29.

The procedure illustrated in FIGS. 27–29 may be facilitated by radiologic observation of radiologic markers provided at any desired location or locations on structure 600. For example, atraumatic end 602 may itself be made of a radiologic material such as gold, platinum, silver, tungsten, or any other suitable substance.

When the condition of the patient is as shown in FIG. 24, 25, or 29, depending on the apparatus and procedural options selected, the patient is ready for installation of a tubular bypass graft along structure 600 between the distal end of structure 300 and the point at which structure 600 passes through the side wall of coronary artery 20.

An illustrative embodiment of a tubular graft 42 and structure 800 for delivering and installing the graft along structure 600 is shown in FIG. 30 (which comprises FIGS. 30a and 30b connected between the right in FIG. 30a and the left in FIG. 30b). It should be understood that the portion of structure 800 that is shown in FIG. 30b remains outside the patient at all times, and that structure 800 may have any desired length between the distal portion shown in FIG. 30a and the proximal portion shown in FIG. 30b. Graft 42 is shown in FIG. 30 with a connector 50 at its proximal end for use in connecting the graft to the side wall of the patient's aorta 30. Connector 50 may be of a type shown in commonly assigned, concurrently filed U.S. patent application Ser. No. 09/187,335 filed Nov. 6, 1998, which is hereby incorporated by reference herein in its entirety. Graft 42 is also shown in FIG. 30 with a connector 60 at its distal end for use in connecting the graft to the patient's coronary artery 20. Connector 60 may be of a type shown in commonly assigned, concurrently filed U.S. patent application Ser. No. 09/187,361, filed Nov. 6, 1998, which is hereby incorporated by reference herein in its entirety.

Graft 42 is assumed to be a length of the patient's saphenous vein which has been harvested for use in the coronary artery bypass procedure being described. It will be understood however, that other natural body conduit can be used for graft 42, or that graft 42 can be a synthetic graft or a combination of natural and synthetic materials. It will also be understood that the particular connectors 50 and 60 shown in FIG. 30 are only illustrative and that other connectors can be used instead if desired. For example, connectors of the type shown in commonly assigned, concurrently filed U.S. patent application Ser. No. 09/186,774 filed Nov. 6, 1998, which is hereby incorporated by reference herein in its entirety, can be used for distal (coronary artery) connector 60. Connectors of the type shown in above-mentioned application Ser. No. 09/187,335 filed Nov. 6, 1998 can also be used for distal connector 60.

Tube 810 is configured for disposition substantially concentrically around structure 600 and for sliding axially along that structure. Tube 810 may be made of stainless steel hypotube so that it can bend laterally to follow whatever straight or curved path structure 600 has in the patient. Tube 810 is axially strong enough to transmit pushing or pulling force between proximal actuator structure 812 and distal tip structure 820, both of which are secured to tube 810 at respective opposite ends thereof. Distal tip structure 820 has a substantially conical distal-most outer surface portion 822 and a more proximal, substantially cylindrical surface portion 824. The cone angle B of conical surface portion 822 is preferably relatively small (e.g., in the range from about 5° to about 15°, more preferably in the range from about 5° to about 10°). This helps structure 820 to gradually enlarge the aperture through the epicardial membrane and the side wall of coronary artery 20 and thereby enter the artery without the artery collapsing as a result of too much force being applied to the exterior. Angle B is sometimes referred to herein as the "cone angle." Tip structure 820 includes an annular recess 826 in its proximal portion for receiving the distal-most portions of structure 830/832 (described below), connector 60, and graft conduit 42.

Tube 830 is disposed substantially concentrically around tube 810 and is slidable axially relative to tube 810. Annular balloon 832 is secured to a distal portion of tube 830. Actuator structure 834 and luer connector 836 are secured to a proximal portion of tube 830. The side wall of tube 830 preferably includes a lumen (not shown) which extends from connection 836 to the interior of balloon 832 so that the balloon can be inflated or deflated by appropriately directed fluid flow through that lumen. Balloon 832 is shown deflated in FIG. 30.

Tube 830 is again sufficiently laterally flexible to allow structure 800 to follow whatever path structure 600 has in the patient. Tube 830 is also axially strong enough to transmit pushing or pulling force axially between balloon 832 and actuator structure 834, although the axial force tube 830 is required to transmit is typically less than the axial force tube 810 must transmit. Examples of suitable materials for tube 830 include polymers such as nylon, Teflon, and polyethylene.

Connector 60 is disposed annularly around balloon 832. In FIG. 30 connector 60 has its initial, relatively small, circumferential size. Fingers 62 extend radially out from the main portion of connector 60 in order to pass through the distal end portion of graft conduit 42 and thereby secure the graft to the connector. Other graft-to-connector securing means such a sutures may be used instead of or in addition to fingers 62. Connector 60 can be plastically circumferentially enlarged by inflation of balloon 832 as described below when tip structure 820 is shifted distally relative to balloon 832 to fully expose elements 832 and 60 and the distal end portion of graft conduit 42. In the condition shown in FIG. 30, however, tip structure 820 shields and protects elements 832, 60, and 42 and provides a smooth profile for facilitating entry of these elements into the patient's coronary artery through an aperture in the side wall of that artery (see the following discussion of use of apparatus 800). Additional details regarding suitable constructions of connector 60 will be found in above-mentioned application Ser. No. 09/187,361 filed Nov. 6, 1998.

The components of structure 800 that have thus far been described are particularly associated with positioning and control of distal connector 60. The further components of structure 800 that will now be described are particularly associated with positioning and control of proximal connector 50.

Tube 840 is disposed substantially concentrically around tube 830. Tube 840 is slidable axially along tube 830 by proximal actuator 842, but preferably includes a proximal structure 844 (e.g., a collet-type structure) for allowing tube 840 to be releasably locked to tube 830 at various axial locations along tube 830. In this way tubes 830 and 840 can be shifted axially relative to one another to accommodate any desired length of graft conduit 42. When structure 800 is thus adjusted for a particular length of graft conduit, structure 844 can be operated to lock tubes 830 and 840 relative to one another for that length of graft.

Annular connector 50 is shown in FIG. 30 in its initially relatively small circumferential size. Connector 50 is resiliently biased to circumferentially enlarge to a larger final circumferential size, but is prevented from doing so by the surrounding distal cone portion 846 of tube 840. Most of connector 50 is disposed annularly around tube 840, but distal portions 52a of the connector enter a proximal-facing annular recess in cone portion 846 which helps to maintain the initial small circumferential size of the connector.

Proximal of portions 52a connector 50 includes radially outwardly extending graft retention fingers 52b that pass through the proximal end portion of graft conduit 42 to secure the connector to the graft conduit. Other graft-to-connector securing means such as sutures can be used instead of or in addition to fingers 52b.

Still more proximal of fingers 52b connector 50 includes "inside" fingers 52c and "outside" fingers 52d. Inside fingers 52c are resiliently biased to spring radially out, but are initially held relatively parallel to the longitudinal axis of structure 800 by being confined inside a distal end portion of tube 850. Outside fingers 52d are also resiliently biased to spring radially out, but are initially held relatively parallel to the longitudinal axis of structure 800 by being confined inside catheter 300 (which is already in place in the patient as shown, for example, in FIG. 25). Tube 850 is disposed substantially concentrically around tube 840 and is axially slidable relative thereto by proximal actuator 852. Tube 860 is disposed substantially concentrically around tube 850 and is axially slidable relative thereto by proximal actuator 862. The distal end of tube 860 is axially aligned with proximal portions of fingers 52d. Each of tubes 840, 850 and 860 is sufficiently laterally flexible so as not to interfere with the ability of structure 800 to follow any path that structures 300 and 600 have in the patient. Each of tubes 840, 850, and 860 is also axially strong enough to transmit necessary forces axially along the tube between the associated proximal actuator 842, 852, or 862 and the operative distal end portion of the tube. As has been mentioned, additional details of suitable constructions for connector 50 can be found in above-mentioned application Ser. No. 09/187,335 filed Nov. 6, 1998.

Figure 31:
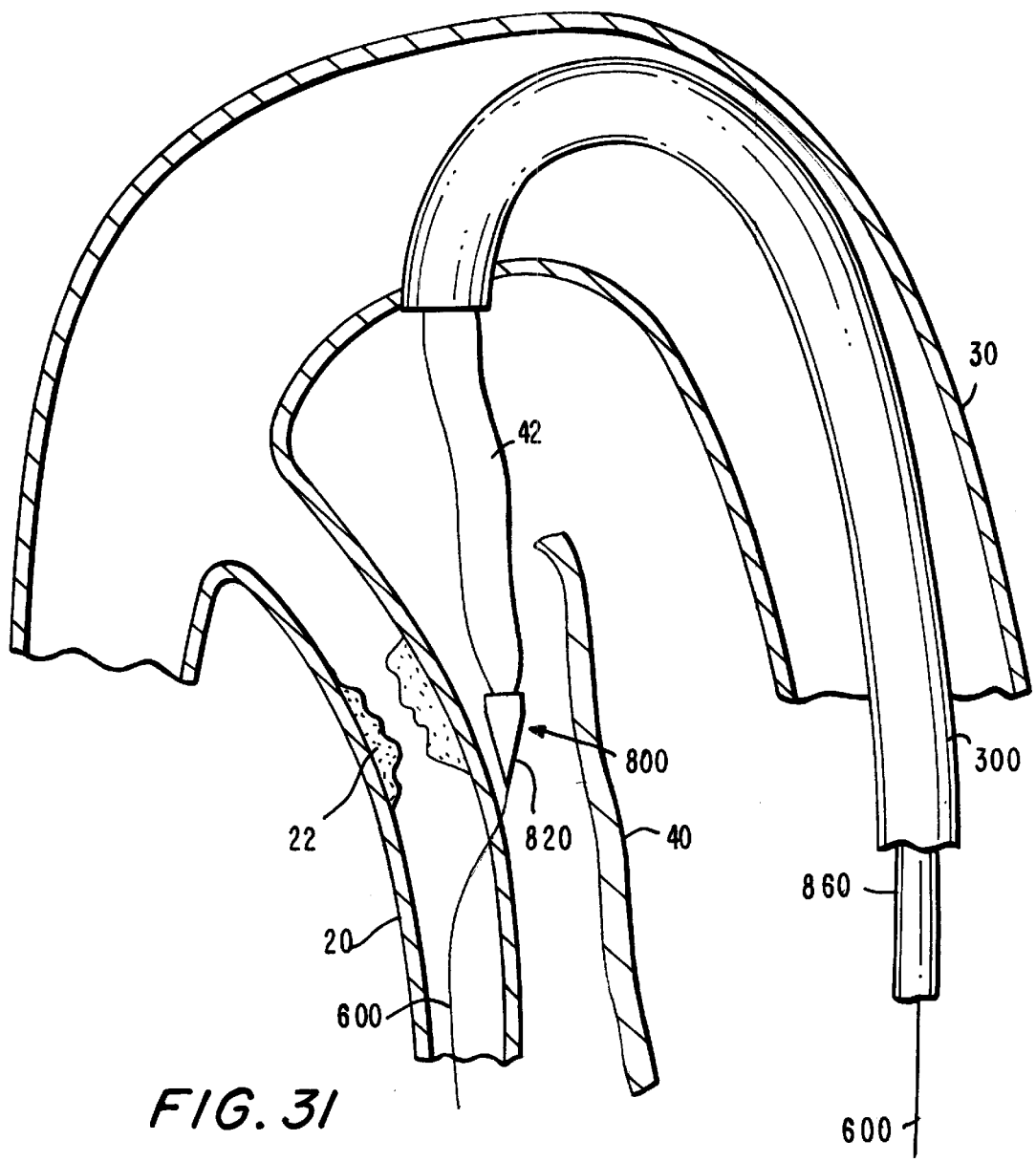
FIG. 31 is a view similar to FIG. 25, but for the alternative shown in FIG. 29, showing use of the apparatus of FIG. 30.

Structure 800, with a suitable length of graft 42 and associated connectors 50 and 60 mounted thereon as shown in FIG. 30, is inserted axially into the patient along structure 600 and inside catheter 300 as shown in FIG. 31. At the distal end of catheter 300, the distal portion of structure 800 emerges from the catheter and therefore from the patient's aorta 30 and continues to follow structure 600 toward the side wall of the patient's coronary artery 20.

Figure 32:
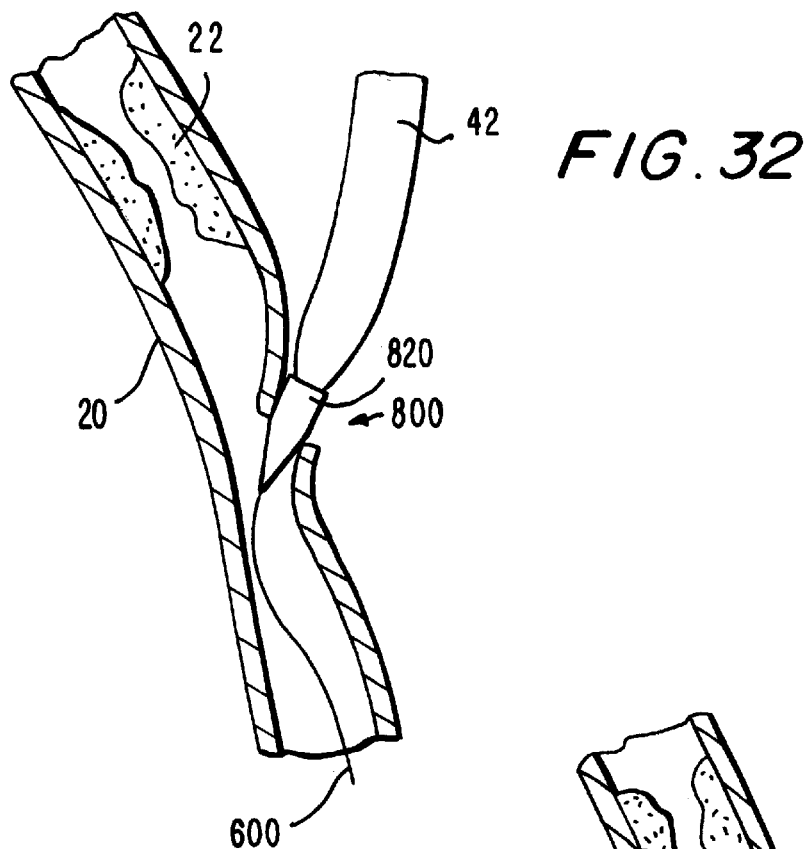
FIG. 32 is a view similar to a portion of FIG. 31 showing a later stage in use of the FIG. 30 apparatus.

Continued distal pushing of structure 800 axially along structure 600 causes the conical distal tip 820 of structure 800 to begin to penetrate the side wall of the coronary artery as shown in FIG. 32, thereby gradually enlarging the aperture in the coronary artery side wall previously occupied solely by structure 600. Structure 800 continues to be pushed distally until distal tip structure 820 is entirely inside the coronary artery, as is connector 60 and the distal portion of graft 42. Then tube 830 is held stationary while tube 810 continues to be pushed distally. This causes distal tip structure 820 to separate from connector 60 and the associated distal portions of graft 42 and structure 830/832 (see FIG. 33).

Figure 33:
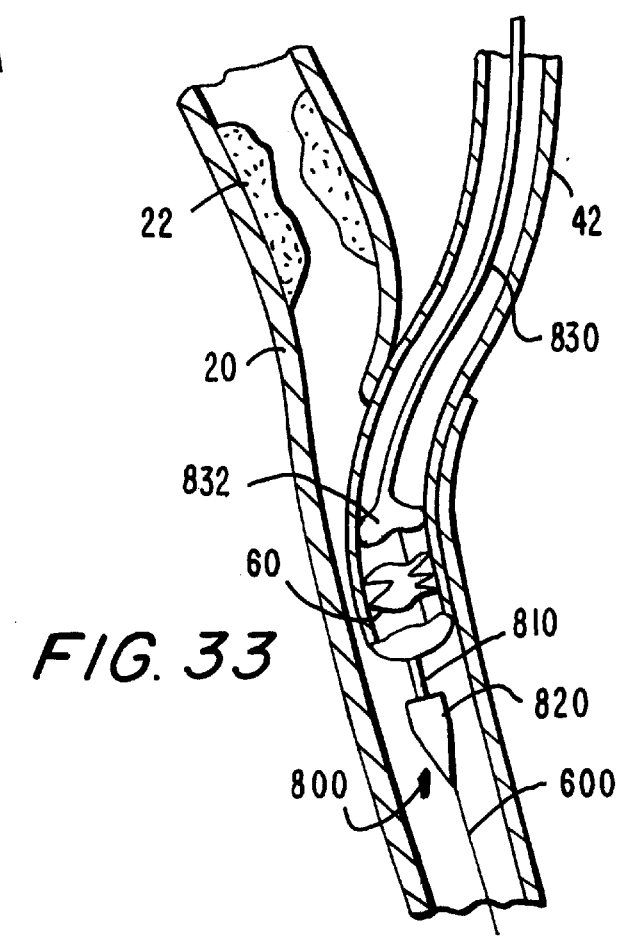
FIG. 33 is a view similar to FIG. 32 showing a stall later stage in use of the FIG. 30 apparatus.

Balloon 832 is then inflated to circumferentially plastically enlarge connector 60 as shown in FIG. 33. Connector 60 thereby presses the surrounding distal portion of graft 42 radially out against the inner surface of the coronary artery wall, which both holds the distal end of the graft inside the coronary artery and provides a hemodynamic seal between the the graft and the coronary artery. If desired, connector 60 can be long enough to extend upstream inside graft 42 and out the aperture in the coronary artery side wall to help hold open the graft where it passes through that aperture and to help the graft seal the aperture. After connector 60 has been thus radially enlarged, balloon 832 can be deflated again.

Figure 34:
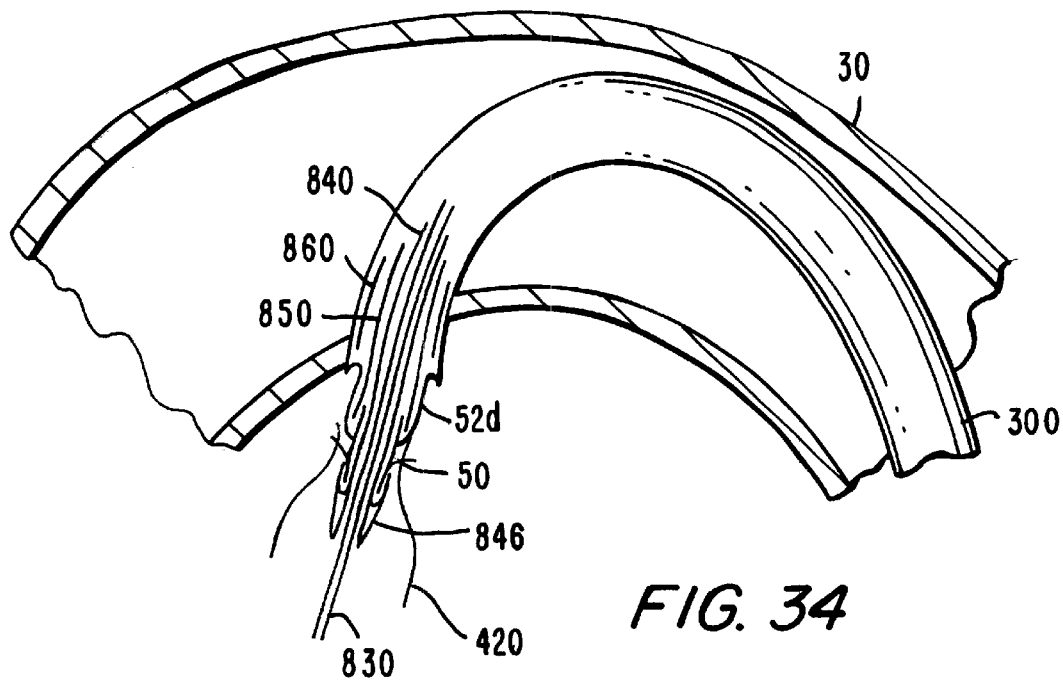
FIG. 34 is a view similar to another portion of FIG. 31 showing a stage in use of the FIG. 30 apparatus comparable to the stage shown in FIG. 33.

FIG. 34 illustrates the condition of the portion of structure 800 in the vicinity of connector 50 when the distal portion of the apparatus is as shown in FIG. 33. In particular, outside fingers 52d of connector 50 are preferably just outside the side wall of aorta 30.

Figure 35:
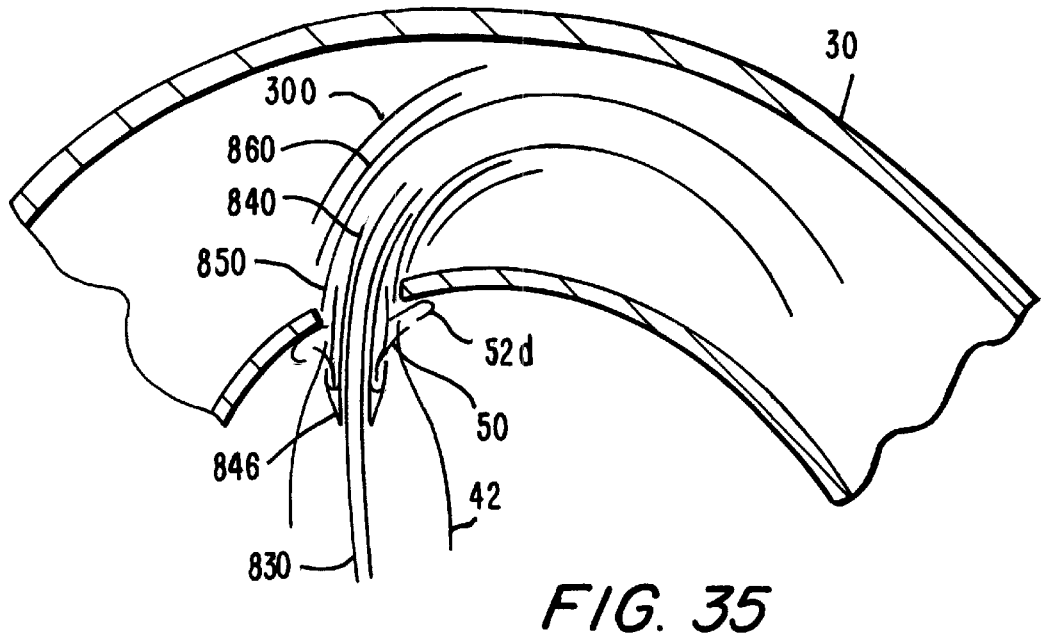
FIG. 35 is a view similar to FIG. 34 showing an even later stage in use of the FIG. 30 apparatus.

The next step is to proximally retract catheter 300 while holding tubes 840, 850, and 860 stationary. This releases outside fingers 52d to spring radially out as shown in FIG. 35. Tube 840 can then be pulled proximally back somewhat to snug fingers 52d up against the wall of aorta 30 as is also shown in FIG. 35.

Figure 36:
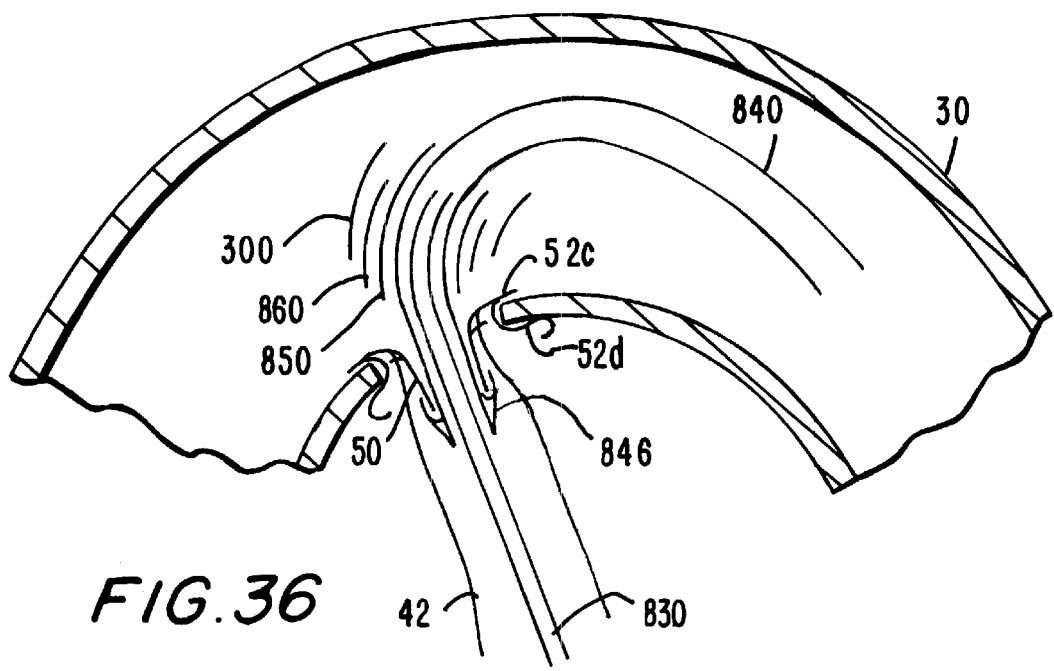
FIG. 36 is a view similar to FIG. 35 showing a still later stage in use of the FIG. 30 apparatus.

The next step is to proximally retract tube 850. This allows inside fingers 52 to spring radially out inside the side wall of the aorta 30 as shown in FIG. 36.

Figure 37:
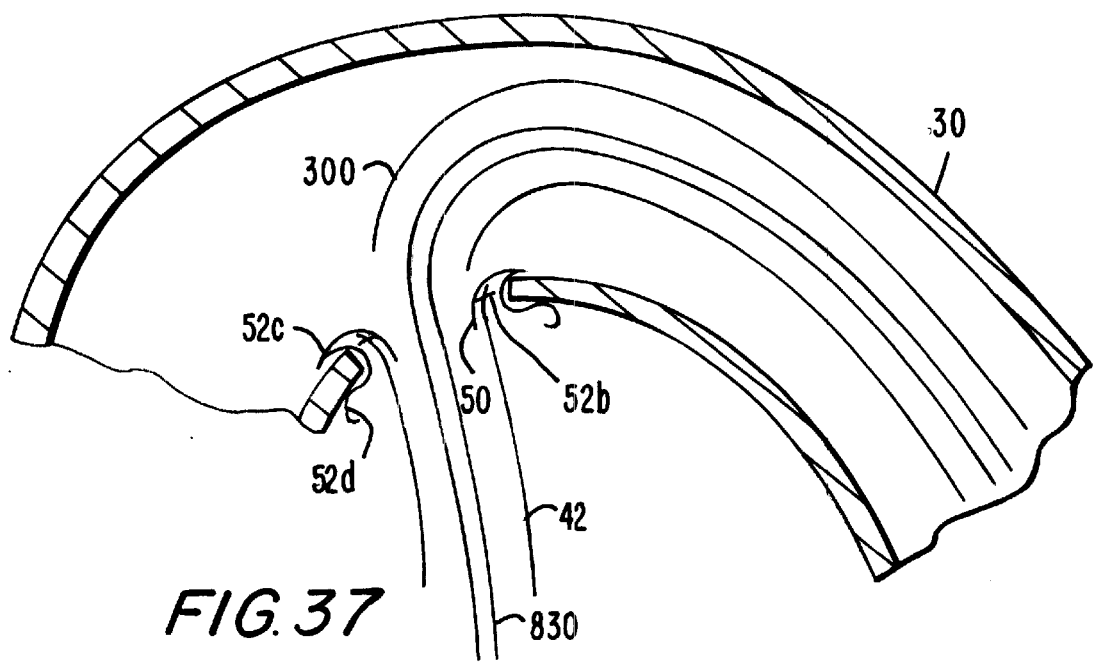
FIG. 37 is a view similar to FIG. 36 showing an even later stage in use of the FIG. 30 apparatus.

The next step is to shift tube 840 distally, which releases connector 50 from the circumferential restraint of the distal portion 846 of that tube. This allows connector 50 to resiliently fully enlarge to its final, relatively large circumference as shown in FIG. 37.

Figure 38:
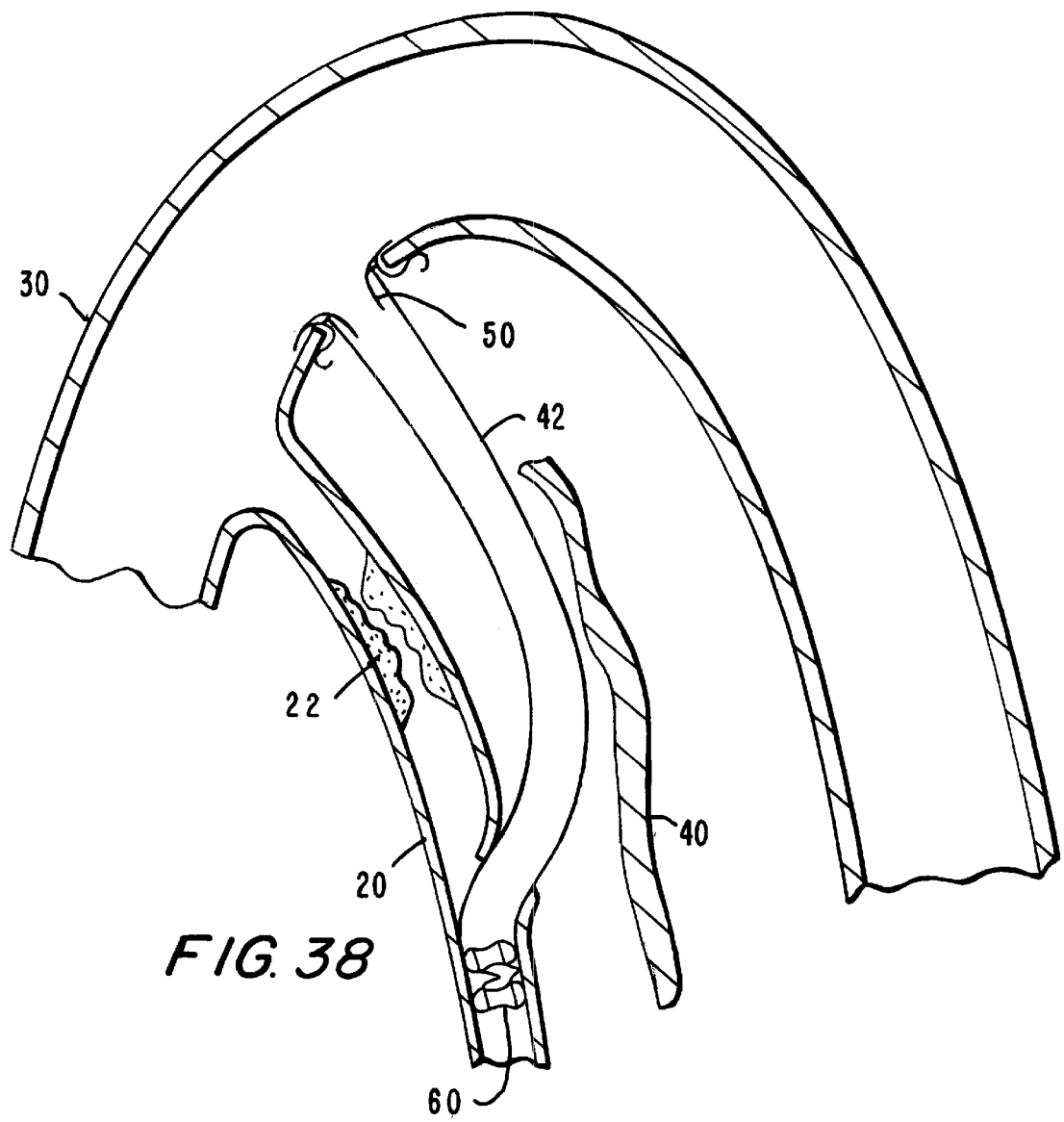
FIG. 38 is a view similar to FIG. 31 showing an illustrative end result of use of the apparatus and methods of this invention.

All of structures 300, 600, and 800 can then be withdrawn proximally from the patient. This leaves the final condition of the patient as shown in FIG. 38, i.e., with connector 50 providing an anastomotic connection between the side wall of aorta 30 and the proximal end of graft conduit 42, and with connector 60 providing an anastomotic connection between the distal end of graft conduit 42 and the inside of coronary artery 20 downstream from occlusion 22. The downstream portion of coronary artery 20 is thereby supplied with aortic blood via bypass graft conduit 42. As much as possible of the work of installing graft 42 has been performed in a minimally invasive way, and in particular via lumens of the patient's circulatory system.

A desirable feature of structure 800 is the fact that the proximal and distal connector delivery components are independent of one another in terms of deployment controls. The distal connector delivery and deployment components are coaxially inside the proximal connector delivery and deployment components. After graft 42 has been attached to connectors 50 and 60, the space between the respectively associated portions of structure 800 can be adjusted to add or remove graft length between the connectors as needed. Structure 844 can then be used to fix this distance once the required space between the connectors is set.

Radiologic markers on structure 800 and/or on connectors 50 and 60 can be used to help the physician properly position these components relative to circulatory system conduits 20 and 30 during the operational steps described above.

It will be noted that the present invention is suitable for adding a new length of graft conduit to a patient's circulatory system between two points on that system that can be quite widely spaced from one another (as in the case of the aorta, on the one hand, and a coronary artery beyond an occlusion, on the other hand). The graft is installed outside the patient's existing circulatory system through the space in the patient between the above-mentioned two endpoints. The graft is installed along a path initially defined by structure 600. The invention does not rely on tunneling through tissue masses in the patient to provide a path for the graft.

It will be understood that the foregoing is only illustrative of the principles of the invention and that various modifications can be made by those skilled in the art without departing from the scope and spirit of the invention. For example, the invention can be used to add a graft to the patient's circulatory system elsewhere than between the aorta and a coronary artery as has been specifically shown and described above. Similarly, although particular examples of connector types have been shown herein, many other forms of connectors can be used instead if desired.

What is claimed is:

1. Instrumentation for facilitating penetration of a side wall of a tubular body tissue conduit from the interior lumen of the conduit comprising:

a tubular structure which is axially insertable into and along the lumen of the conduit and which has an axial portion configured to deflect toward a first portion of the interior surface of the side wall from a second portion of the interior surface of the side wall which is axially spaced from the first portion and on the side of the side wall which is substantially opposite the first portion, the tubular structure having an axially extending interior passageway with an opening to the exterior of the tubular structure adjacent the first portion; and a laterally flexible, longitudinal, tissue piercing structure configured to pierce a side wall of the tubular body tissue conduit and to project from the side wall through any adjacent tissue outside of the tubular body tissue conduit, wherein said tissue piercing structure is axially insertable into and along the passageway and which is axially reciprocable relative to the tubular structure so that it exits the opening toward the first portion when moved toward the opening;

wherein the axial portion is an axially medial portion of the tubular structure which is configured to arch toward the first portion from the second portion and from a third portion of the interior surface of the side wall which is on the same side of the side wall as the second portion, the second and third portions being axially spaced from the first portion in respective opposite axial directions from the first portion.

2. The instrumentation defined in claim 1, wherein the opening is a lateral branch of the passageway which extends in both axial directions past the opening.

3. Apparatus for use in forming an aperture in a side wall of a tubular body tissue conduit from the interior lumen of the conduit comprising:

a first tubular structure which is axially insertable into and along the lumen of the conduit and which has a distal portion configured to penetrate and pass through the side wall of the conduit from the interior of the lumen through any adjacent tissue outside of the tubular body tissue conduit;

a longitudinal structure which is axially extendable from the distal portion of the first structure, the longitudinal structure being laterally flexible to a degree that it is substantially unable to penetrate body tissue when unsupported by other structure; and an annular tissue cutting structure disposed annularly around the first structure and being extendable through the side wall of the conduit to cut through the side wall annularly around the first structure, the tissue cutting structure being guidable by the longitudinal structure which is extendable from the first portion to substantially prevent the tissue cutting structure from cutting additional tissue outside the side wall of the conduit.

4. The apparatus defined in claim 3 wherein the longitudinal structure is axially extendable from an interior lumen of the first structure.

5. The apparatus defined in claim 3 wherein each of the longitudinal structure and the tissue cutting structure is independently axially movable relative to the first structure.

6. The apparatus defined in claim 3 wherein an outer surface portion of the first structure is configured to retain on the first structure an annulus of tissue cut from the side wall by the tissue cutting structure.

7. The apparatus defined in claim 3 further comprising:
a second tubular structure disposed annularly around the tissue cutting structure and extendable into and through an aperture formed in the side wall by the tissue cutting structure.

8. The apparatus defined in claim 7 further comprising:
an inflatable annular balloon which extends annularly around an outer surface portion of the second structure for restricting axial shifting of the second structure when the balloon is inflated and contacts the side wall.

9. The apparatus defined in claim 7 further comprising:
first and second inflatable annular balloons which extend annularly around respective first and second, axially spaced, outer surface portions of the second structure for respectively resiliently bearing on annular portions of inner and outer surfaces of the side wall when the second structure is positioned so that the balloons are on respective sides of the side wall and the balloons are inflated.

10. A method of forming an aperture in a side wall of a tubular body tissue conduit from the interior lumen of the conduit comprising:
inserting a first tubular structure axially into and along the lumen of the conduit;
causing a distal portion of the first structure to penetrate and pass through the side wall of the conduit from the interior of the lumen through any adjacent tissue outside of the tubular body tissue conduit;
axially extending a longitudinal structure from the distal portion of the first structure, the longitudinal structure being laterally flexible to a degree that it is substantially unable to penetrate body tissue when unsupported by other structure; and
axially extending an annular tissue cutting structure, which is annularly disposed around the first structure, through the side wall of the conduit to cut through the side wall of the conduit annularly around the first structure.

11. The method defined in claim 10 further comprising:
axially extending a second tubular structure, which is annularly disposed around the tissue cutting structure, into and through an aperture formed in the side wall by the tissue cutting structure.

12. An elongated, catheter-like, medical instrument configured for axial insertion into a patient's body comprising an elongated shaft having (1) a proximal portion which is laterally flexible in response to external forces applied laterally to the shaft and which is configured to transmit torque along a longitudinal axis of the shaft, and (2) a distal portion which is laterally deflectable by lateral deflection forces transmitted axially along the proximal portion via lateral deflection force transmitting structure included in the proximal portion, the proximal portion being substantially laterally undeflected by lateral deflection forces transmitted by the lateral deflection force transmitting structure, and the shaft have a lumen which extends axially along the proximal and distal portions.

13. The instrument defined in claim 12 further comprising:
an elongated structure disposed in said lumen for axial reciprocation relative to said shaft.

14. The instrument defined in claim 13 wherein the elongated structure has a distal part configured to extend distally from a distal end of the lumen.

15. The instrument defined in claim 14 wherein the distal part is additionally configured for proximal retraction into the lumen.

16. The instrument defined in claim 14 wherein the distal part includes a loop.

17. The instrument defined in claim 14 wherein the distal part comprises a hook.

18. The instrument defined in claim 13 wherein the elongated structure comprises a radiologic material.

19. The instrument defined in claim 12 further comprising:
image transmitting structure disposed in the lumen for transmitting image information axially along the shaft.

20. The instrument defined in claim 12 further comprising:
light transmitting structure disposed in the lumen for transmitting light axially along the shaft.

21. The instrument defined in claim 12 wherein the lumen is configured to transmit fluid axially along the shaft.

22. The instrument defined in claim 12 further comprising:
releasable locking structure operatively associated with a proximal end part of the proximal portion and configured to releasably lock a desired amount of lateral deflection force into the lateral deflection force transmitting structure.

23. Apparatus for use in penetrating a side wall of a tubular body tissue conduit from the interior lumen of the conduit comprising:
a longitudinal structure configured for axial insertion into and along the lumen of the conduit and including a first relatively distal portion having a first relatively low lateral stiffness and a second relatively proximal portion having a second relatively high lateral stiffness, wherein gradual transition is provided between the second relatively proximal portion and the first relatively distal portion at the second relatively proximal portion's distal end, the first portion having a distal tip which is configured to facilitate penetration of the side wall of the conduit through any adjacent tissue outside of the tubular body tissue conduit.

24. The apparatus defined in claim 23 wherein a typical cross section of the first portion is relatively small and a typical cross section of the second portion is relatively large.

25. The apparatus defined in claim 23 wherein the longitudinal structure comprises a radiologic material.

26. The apparatus defined in claim 23 further comprising:
a radiologic marker on the first portion.

27. The apparatus defined in claim 26 wherein the radiologic marker comprises radiologic material disposed annularly about the first portion.

28. The apparatus defined in claim 27 wherein the radiologic material comprises wire wrapped around the first portion.

29. The apparatus defined in claim 27 wherein the first portion comprises an exterior surface part for providing a substantially smooth exterior surface transition from a location distal of the marker to an exterior surface of the marker.

30. The apparatus defined in claim 27 wherein the first portion includes a channel extending annularly around the first portion, and wherein the marker comprises an annulus of radiologic material disposed in the channel.

31. The apparatus defined in claim 23 wherein the first portion includes a longitudinal section which is resiliently biased to deflect laterally when unsupported by other structure.

32. The apparatus defined in claim 23 wherein the first portion includes a longitudinal section which is laterally bifurcated to reduce its stiffness.

33. The apparatus defined in claim 32 wherein portions of the longitudinal section on opposite sides of the bifurcation are resiliently biased to spring apart from one another when not confined by other structure.

34. The apparatus defined in claim 33 wherein the portions of the longitudinal section on opposite sides of the bifurcation form an open loop when they spring apart from one another.

35. The apparatus defined in claim 33 further comprising:
a hooking structure configured for disposition outside the conduit, and further configured to engage the longitudinal structure by hooking one of the portions of the longitudinal structure on opposite sides of the bifurcation when those portions are separated from one another.

36. The apparatus defined in claim 23 wherein the distal tip of the first portion is sharply pointed in the distal direction to facilitate penetration of the side wall of the conduit.

37. The apparatus defined in claim 23 further comprising:
a longitudinal support structure configured for axial insertion into and along the lumen of the conduit substantially parallel to the longitudinal structure, the support structure being configured to laterally support at least a portion of the longitudinal structure while permitting the longitudinal structure to move axially relative to the support structure.

38. The apparatus defined in claim 37 wherein the support structure is configured to guide the distal tip of the longitudinal structure toward the side wall of the conduit.

39. The apparatus defined in claim 38 wherein the support structure includes a longitudinal section which is configured to laterally deflect toward the side wall of the conduit to guide the distal tip of the longitudinal structure toward the side wall.

40. The apparatus defined in claim 39 wherein the longitudinal section of the support structure is resiliently biased to laterally deflect toward the side wall of the conduit.

41. The apparatus defined in claim 39 wherein the longitudinal section of the support structure is a longitudinal medial section of the support structure.

42. The apparatus defined in claim 41 wherein the longitudinal section is configured to arch transversely in the lumen of the conduit between opposite portions of the side wall of the conduit.

43. The apparatus defined in claim 42 wherein the arch has an apex, and wherein the support structure is configured to guide the distal tip of the longitudinal structure toward the side wall of the conduit adjacent the apex.

44. The apparatus defined in claim 37 further comprising:
a longitudinal guide structure configured for axial insertion into and along the lumen of the conduit, and further configured to guide the support structure into and along the lumen of the conduit substantially parallel to guide structure.

45. The apparatus defined in claim 44 wherein the support structure is configured for removal of the guide structure after the guide structure has guided the support structure into and along the lumen of the conduit.

46. The apparatus defined in claim 45 wherein the support structure is configured to substantially conform to alignment of the guide structure during guidance by the support structure.

47. The apparatus defined in claim 46 wherein a longitudinal section of the first portion of the longitudinal structure is configured to deflect laterally in the lumen of the conduit when the guide structure is removed.

48. The apparatus defined in claim 45 wherein the support structure is configured to receive the longitudinal structure substantially in place of the guide structure after the guide structure has been removed.

49. Apparatus for use in medical treatment of a patient's tubular body conduit comprising:
an elongated, laterally flexible but resilient structure having (1) an axially medial portion configured for axial insertion into and along a lumen of the body conduit and also for axial reciprocation through an aperture in a side wall of the body conduit, and (2) an axially distal portion configured for passage along the lumen of the body conduit in either axial direction along that lumen from the aperture;
wherein the distal portion is radially enlarged relative to the medial portion; and
the distal portion is approximately ball-shaped.

50. A method of positioning an elongated, laterally flexible but resilient structure relative to a body conduit in a patient comprising:
initially positioning the structure relative to the body conduit so that an axially distal portion of the structure extends axially along the lumen inside a first length of the conduit that extends axially in a first direction from an aperture in a side wall of the conduit, and so that a proximal portion of the structure extends out through the aperture and axially along a path that extends back along the outside of the first length of the conduit;
pulling the proximal portion in the proximal direction until the amount of the distal portion that remains inside the first length of the conduit is too short to be guided by the first length of the conduit and therefore resiliently shifts into the lumen inside a second length of the conduit that extends axially in a second direction from the aperture; and
pushing the proximal portion in the distal direction to cause the distal portion to extend farther along the lumen inside the second length of the conduit.

51. Apparatus for inserting a tubular graft into a side wall of a tubular body tissue conduit from outside the conduit comprising:
a hollow tubular shaft structure configured to receive a longitudinal guide structure axially along a lumen inside the shaft structure so that the shaft structure and the guide structure can slide axially relative to one another; and a substantially conical tip structure disposed on an axial end portion of the shaft structure substantially concentrically with the shaft structure so that an apex of the conical tip structure points axially away from the shaft structure, an axial continuation of the lumen inside the shaft structure extending through the tip structure and out at the apex so that the guide structure can extend through the axial continuation and can slide axially relative to the axial continuation, the shaft structure being configured to receive the graft annularly around the shaft structure, and the tip structure including an annular recess which extends substantially annularly around the shaft structure, the recess being open in a direction that points away from the apex, and the recess having a radially outer side wall that is radially spaced from the shaft structure by an amount sufficient to allow an annular axial end portion of the graft to be received in the recess with the outer side wall radially outside the portion of the graft that is thus received in the recess; wherein the shaft structure is connected to the tip structure so that the shaft structure can be used to push the tip structure in the direction of its apex.

52. Apparatus for inserting a tubular graft into a side wall of a tubular body tissue conduit from outside the conduit comprising:
a hollow tubular shaft structure configured to receive a longitudinal guide structure axially along a lumen inside the shaft structure so that the shaft structure and the guide structure can slide axially relative to one another;
a substantially conical tip structure disposed on an axial end portion of the shaft structure substantially concentrically with the shaft structure so that an apex of the conical tip structure points axially away from the shaft structure, an axial continuation of the lumen inside the shaft structure extending through the tip structure and out at the apex so that the guide structure can extend through the axial continuation and can slide axially relative to the axial continuation, the shaft structure being configured to receive the graft annularly around the shaft structure, and the tip structure including an annular recess which extends substantially annularly around the shaft structure, the recess being open in a direction that points away from the apex, and the recess having a radially outer side wall that is radially spaced from the shaft structure by an amount sufficient to allow an annular axial end portion of the graft to be received in the recess with the outer side wall radially outside the portion of the graft that is thus received in the recess; and
a radially expandable structure disposed substantially annularly around the shaft structure inside a graft around the shaft structure, wherein the expandable structure is movable along the shaft structure.

53. Apparatus for inserting a tubular graft into a side wall of a tubular body tissue conduit from outside the conduit comprising:
a hollow tubular shaft structure configured to receive a longitudinal guide structure axially along a lumen inside the shaft structure so that the shaft structure and the guide structure can slide axially relative to one another;
a substantially conical tip structure disposed on an axial end portion of the shaft structure substantially concentrically with the shaft structure so that an apex of the conical tip structure points axially away from the shaft structure, an axial continuation of the lumen inside the shaft structure extending through the tip structure and out at the apex so that the guide structure can extend through the axial continuation and can slide axially relative to the axial continuation, the shaft structure being configured to receive the graft annularly around the shaft structure, and the tip structure including an annular recess which extends substantially annularly around the shaft structure, the recess being open in a direction that points away from the apex, and the recess having a radially outer side wall that is radially spaced from the shaft structure by an amount sufficient to allow an annular axial end portion of the graft to be received in the recess with the outer side wall radially outside the portion of the graft that is thus received in the recess; and
a radially expandable structure disposed substantially annularly around the shaft structure inside a graft around the shaft structure, wherein the graft is movable along the shaft structure.

54. Apparatus for adding a tubular graft conduit to a patient's existing circulatory system between first and second points on the circulatory system that are spaced from one another by a space in the patient comprising:
a first longitudinal shaft structure configured to emerge axially from inside the circulatory system at the second point and to move axially through the space to the first point, the first shaft structure having a distal tip structure which is configured to penetrate the circulatory system at the first point and to pass substantially coaxially inside the circulatory system adjacent the first point;
a graft conduit disposed substantially coaxially around the first shaft structure proximal of the distal tip structure, the graft conduit having a first annular connector on its first end adjacent the distal tip structure and a second annular connector on its second end remote from the distal tip structure, the first connector being initially circumferentially small enough to at least partly follow the distal tip structure into the circulatory system adjacent the first point substantially coaxially with the circulatory system at that point;
a first connector deployment structure disposed adjacent to the first connector and configured to selectively circumferentially enlarge the first connector to cause the first connector to secure the first end of the graft conduit to the circulatory system substantially coaxially in the circulatory system adjacent the first point; and
a second connector deployment structure disposed adjacent to the second connector and configured to cause the second connector to connect the second end of the graft conduit to the circulatory system at the second point.

55. The apparatus defined in claim 54 wherein the distal tip structure includes an annular recess substantially coaxial with the first shaft structure and configured to receive at least a portion of the first connector and an adjacent portion of the graft conduit.

56. The apparatus defined in claim 54 wherein the first connector deployment structure comprises a selectively inflatable balloon.

57. The apparatus defined in claim 56 wherein the balloon is disposed on a second longitudinal shaft structure that is disposed substantially coaxially around the first shaft structure and that is axially movable relative to the first shaft structure.

58. The apparatus defined in claim 54 wherein the second connector has an initially relatively small circumference and is resiliently biased to enlarge to a relatively large final circumference.

59. The apparatus defined in claim 58 wherein the second connector deployment structure is configured to maintain the second connector in its initially relatively small circumference and to selectively release the second connector so that it can resiliently enlarge to its relatively large final circumference.

60. The apparatus defined in claim 59 wherein the second connector includes first and second, axially spaced, annular arrays of fingers that are resiliently biased to project radially out from remaining structure of the second connector, and wherein the second connector deployment structure is further configured to initially prevent the fingers from projecting radially out.

61. The apparatus defined in claim 60 wherein the second connector deployment structure is still further configured to selectively release the first and second arrays individually.

62. The apparatus defined in claim 61 wherein the second connector deployment structure is still further configured to maintain the remaining structure of the second connector in the initially relatively small circumference independent of release of the first and second arrays, and to selectively release the remaining structure so that it can resiliently enlarge to its relatively large final circumference.

63. The apparatus defined in claim 59 wherein the second connector deployment structure comprises a tubular structure disposed substantially concentrically around the first shaft structure and around at least part of the second connector for initially maintaining the second connector in its initially relatively small circumference.

64. The apparatus defined in claim 63 wherein the tubular structure is axially movable relative to the first shaft structure and the second connector in order to release the second connector so that it can resiliently enlarge to its relatively large final circumference.

65. The apparatus defined in claim 64 wherein the second connector includes a main body and first and second, axially spaced, annular arrays of fingers that are resiliently biased to project radially out from the main body, and wherein the tubular structure comprises:
    first, second, and third substantially concentric tubes for respectively maintaining the first and second arrays and the main body in an initially relatively small circumference, each of the tubes being axially movable to selectively release the first and second arrays and the main body for resilient circumferential enlargement.

66. The apparatus defined in claim 54 wherein the second connector deployment structure is still further configured to selectively pull the second connector in a direction away from the first point toward the second point.

67. The apparatus defined in claim 54 wherein the first and second connector deployment structures are movable relative to one another axially along the first shaft structure, and wherein the apparatus further comprises:
    a lock structure for selectively locking the first and second connector deployment structures axially relatively one another.

68. The apparatus defined in claim 67 wherein the lock structure is operable with the first and second connector deployment structures having any of a plurality of different axial spacings.

69. The apparatus defined in claim 54 further comprising:
    a guide structure configured to extend through the space between the first and second points and to guide the first shaft structure from the second point to the first point.

70. The apparatus defined in claim 69 wherein the first shaft structure is further configured for disposition annularly around the guide structure and for sliding axially along the guide structure.

71. The method of attaching a tubular graft to a patient's existing tubular body conduit at a predetermined point along the length of that conduit comprising:
    the lumen introducing a longitudinal structure axially into the lumen of the conduit so that the longitudinal structure initially passes along the lumen to reach the predetermined point from a first direction along the conduit and passes out through the side wall of the conduit through any adjacent tissue outside of the tubular body tissue conduit at the predetermined point;
    re-routing at least a portion of the longitudinal structure inside the lumen so that that portion extends from the predetermined point in a second direction along the conduit, the second direction being substantially opposite to the first direction;
    using the longitudinal structure to guide the graft to the predetermined point from outside the conduit; and
    securing the graft to the conduit adjacent the predetermined point.

72. The method defined in claim 71 further comprising:
    removing the longitudinal structure from the patient.

73. The method defined in claim 71 wherein the using comprises:
    disposing the graft annularly around a part of the longitudinal structure which passes out through the side wall of the conduit; and
    shifting the graft axially along that part of the longitudinal structure toward the predetermined point.

74. The method defined in claim 71 wherein the securing comprises:
    forming an anastomotic connection between the conduit and the graft so that the patient's body fluid can flow between the lumen of the conduit and the interior of the graft.

75. The method defined in claim 74 wherein the securing comprises:
    deploying a mechanical connector to secure the graft to the conduit adjacent the predetermined point.

76. The method defined in claim 71 further comprising:
    passing a part of the longitudinal structure which passes out through the side wall of the conduit at the predetermined point back into a portion of the patient's conduit system at a predetermined location which is spaced along the conduit system from the predetermined point, the longitudinal structure then passing along the interior of the conduit system until it exits from the patient at a remote location.

77. The method defined in claim 76 wherein the using comprises:
    disposing the graft annularly around the longitudinal structure outside the patient adjacent the remote location; and
    shifting the graft axially along the longitudinally structure so that it successively enters the patient at the remote location, travels along the interior of the conduit system toward the predetermined location, emerges from the conduit system at the predetermined location, and extends from the predetermined location to the first location.

78. The method defined in claim 77 further comprising:
    attaching the graft to the conduit system at the predetermined location.

79. The method defined in claim 78 wherein the attaching comprises:

forming an anastomotic connection between the conduit system and the graft so that the patient's body fluid can flow between the interior of the conduit system and the interior of the graft.

80. The method defined in claim 79 wherein the attaching comprises:

deploying a mechanical connector to secure the graft to the conduit adjacent the predetermined location.

81. Apparatus for attaching a tubular graft graft to a patient's existing tubular body conduit at a predetermined point along the length of that conduit comprising:

a longitudinal structure configured for axial introduction to the lumen of the conduit so that the longitudinal structure initially passes along the lumen to the predetermined point from a first direction along the conduit and passes through the side wall of the conduit at the predetermined point through any adjacent tissue outside of the tubular body tissue conduit, the longitudinal structure being further configured for re-routing of at least a portion of that structure inside the lumen so t at that portion extends from the predetermined point in a second direction along the conduit, the second direction being opposite to the first direction; and a graft delivery structure configured to convey the graft axially along the longitudinal structure from outside the conduit into engagement with the conduit at the predetermined point.

82. The apparatus defined in claim 81 wherein the graft delivery structure is further configured to annularly enlarge an opening in the side wall of the conduit initially occupied by the longitudinal structure where the longitudinal structure passes out through the side wall at the predetermined point.

83. The apparatus defined in claim 81 further comprising:

a connector deploying structure configured to deploy a connector for securing the graft to the conduit adjacent the predetermined point.

84. The apparatus defined in claim 83 further comprising:

a substantially annular connector configured for deployment by the connector deploying structure substantially concentric with an axial end portion of the graft.

85. The apparatus defined in claim 84 wherein the connector is further configured to produce a substantially annular connection between the conduit and the graft when deployed by the connector deploying structure.

86. The apparatus defined in claim 84 wherein the connector deploying structure and the connector are further configured for conveyance toward the conduit along the longitudinal structure from outside the conduit.

87. The apparatus defined in claim 81 wherein a part of the longitudinal structure that passes out through the side wall of the conduit at the predetermined point is configured to pass back into a portion of the patient's conduit system at a predetermined location which is spaced along the conduit system from the predetermined point, that part of the longitudinal structure being further configured to pass along the interior of the conduit system until it exits from the patient at a remote location.

88. The apparatus defined in claim 87 wherein the graft delivery structure is further configured to convey the graft axially along the longitudinal structure from outside the patient adjacent the remote location, into the patient at the remote location, along the interior of the conduit system toward the predetermined location, and at least partly out of the conduit system at the predetermined location.

89. The apparatus defined in claim 88 further comprising:

a connecter deploying structure configured to deploy a connector for securing the graft to the conduit system at the predetermined location.

90. The apparatus defined in claim 89 further comprising:

a substantially annular connector configured for deployment by the connector deploying structure substantially concentric with an axial end portion of the graft.

91. The apparatus defined in claim 90 wherein the connector is further configured to produce a substantially annular connection between the conduit system and the graft when deployed by the connector deploying structure.

92. The apparatus defined in claim 90 wherein the connector deploying structure and the connector are further configured for conveyance toward the predetermined location along the longitudinal structure from outside the patient adjacent the remote location.

* * * * *